(12) United States Patent
McAnany

(10) Patent No.: US 11,712,159 B2
(45) Date of Patent: Aug. 1, 2023

(54) METHODS AND DIAGNOSTIC TOOLS FOR MEASURING VISUAL NOISE-BASED CONTRAST SENSITIVITY

(71) Applicant: THE BOARD OF TRUSTEES OF THE UNIVERSITY OF ILLINOIS, Urbana, IL (US)

(72) Inventor: James Jason McAnany, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 118 days.

(21) Appl. No.: 16/768,493

(22) PCT Filed: Nov. 28, 2018

(86) PCT No.: PCT/US2018/062798
§ 371 (c)(1),
(2) Date: May 29, 2020

(87) PCT Pub. No.: WO2019/108617
PCT Pub. Date: Jun. 6, 2019

(65) Prior Publication Data
US 2020/0383562 A1 Dec. 10, 2020

Related U.S. Application Data

(60) Provisional application No. 62/593,306, filed on Dec. 1, 2017.

(51) Int. Cl.
*A61B 3/02* (2006.01)
*A61B 3/00* (2006.01)
*A61B 3/06* (2006.01)

(52) U.S. Cl.
CPC ............ *A61B 3/022* (2013.01); *A61B 3/0033* (2013.01); *A61B 3/0041* (2013.01); *A61B 3/06* (2013.01)

(58) Field of Classification Search
CPC ..... A61B 3/022; A61B 3/0033; A61B 3/0041; A61B 3/06
See application file for complete search history.

(56) References Cited

U.S. PATENT DOCUMENTS 5,461,435 A * 10/1995 Rootzen .................. A61B 3/024
351/224
2004/0036840 A1* 2/2004 Marino .................. A61B 3/028
351/239

(Continued)

FOREIGN PATENT DOCUMENTS

WO 02076301 10/2002
WO 2017089681 6/2017

OTHER PUBLICATIONS

International Search Report and Written Opinion dated Feb. 26, 2019 for PCT Patent Application No. PCT/US2018/062798.

(Continued)

*Primary Examiner* — William R Alexander
*Assistant Examiner* — Sharrief I Broome
(74) *Attorney, Agent, or Firm* — Thomas | Horstemeyer, LLP

(57) ABSTRACT

Methods and diagnostic tools are provided for assessing contrast sensitivity in a subject in the presence and absence of luminance noise by: i) presenting to the subject a series of scenes, each scene comprising at least a first target having a preselected level of contrast superimposed on a uniform background and a second target having a preselected level of contrast superimposed on a luminance noise background, wherein in each successively presented scene the first and second targets that are superimposed on the uniform back-
(Continued)

ground and on the luminance noise background, respectively, have contrast levels that are different from the contrast levels of the first and second targets superimposed on the uniform background and on the luminance noise background, respectively, in the previously presented scene; ii) monitoring responses by the subject to step i); and iii) evaluating the contrast sensitivity of the subject based on the monitored responses.

20 Claims, 18 Drawing Sheets

(56) References Cited

U.S. PATENT DOCUMENTS

| | | | | |
|---|---|---|---|---|
| 2007/0064197 | A1* | 3/2007 | Marino | A61B 3/022 351/229 |
| 2010/0283969 | A1* | 11/2010 | Cooperstock | A61B 3/022 351/201 |
| 2011/0063571 | A1* | 3/2011 | Duffy | A61B 3/06 351/239 |
| 2011/0066069 | A1* | 3/2011 | Duffy | G16H 40/63 600/558 |
| 2015/0150444 | A1* | 6/2015 | Bex | A61B 3/06 351/242 |
| 2020/0178789 | A1* | 6/2020 | Zhu | A61B 3/0041 |

OTHER PUBLICATIONS

Pelli, Denis G; et al. "Using visual noise to characterize amblyopic letter identification " Journal of vision 4.10 (2004): 6-6.
Jason McAnany "Apparatus and method for noise-based visual sensitivity measurement" UIC Office of Technology Management Technology Screening Report Power-point University of Illinois at Chicago (2016) p.p. 1-16.
McAnany, J. Jason; et al. "Reduced contrast sensitivity is associated with elevated equivalent intrinsic noise in type diabetics who have mild or no retinopathy." Investigative ophthalmology & visual science 59.6 (2018): 2652-2658.
McAnany, J. Jason, et al. "Equivalent intrinsic noise, sampling efficiency, and contrast sensitivity in patients with retinitis pigmentosa." Investigative ophthalmology & visual science 54.6 (2013): 3857-3862.
Berson, Eliot L. "Retinitis pigmentosa. The friedenwald lecture." Investigative ophthalmology & visual science 34.5 (1993): 1659-1676.
Grover, Sandee, et al. "Visual acuity impairment in patients with retinitis pigmentosa." Ophthalmology 103.10 (1996) 1593-1600.
Lindberg, C. Ronald, et al. "Contrast sensitivity in retinitis pigmentosa." British Journal of Ophthalmology 65.12 (1981): 855-858.
Alexander, Kenneth R., et al. "Contrast sensitivity deficits in inferred magnocellular and parvocellular pathways in retinitis pigmentosa." Investigative Ophthalmology & Visual Science 45.12 (2004): 4510-4519.
Alexander, Kenneth R.; et al. "Visual acuity vs letter contrast sensitivity in retinitis pigmentosa." Vision research 35.10 (1995): 1495-1499.
Alexander, Kenneth R.; et al. "Coherence and the judgment of spatial displacements in retinitis pigmentosa." Vision research 39.13 (1999): 2267-2274.
Alexander, Kenneth R., et al. "Grating, vernier, and letter acuity in retinitis pigmentosa." Investigative ophthalmology & visual science 33.12 (1992): 3400-3406.
Alexander, Kenneth R., et al. "Discrimination of spatial displacements by patients with retinitis pigmentosa." Vision research 38.8(1998): 1171-1181.
Hall, Cierra, et al. "Effect of luminance noise on the object frequencies mediating letter identification." Frontiers in psychology 5 (2014): 663.

Pelli, Denis G.,; et al. "Why use noise? " JOSA A 16.3 (1999): 647-653.
McAnany, J. Jason; et al. "Spatial contrast sensitivity in dynamic and static additive luminance noise." Vision Research 60.19 (2010): 1957-1965.
Brainard, David H. "The psychophysics toolbox." Spatial vision 10.4 (1997): 433-436.
McAnany, J. Jason; et al. "Contrast sensitivity for letter optotypes vs. gratings under conditions biased toward parvocellular and magnocellular pathways." Vision Research 46.10 (2006): 1574-1584.
Legge, Gordon E.; et al. "Contrast discrimination in noise." JOSA A 4.2 (1987): 391-404.
McAnany, J. Jason,; et al. "Contrast thresholds in additive luminance noise: Effect of noise temporal characteristics." Vision research 49.11 (2009): 1389-1396.
Manahilov, Velitchko; et al. "Temporal properties of the visual responses to luminance and contrast modulated noise." Vision research 43.17 (2003): 1855-1867.
Lu, Zhong-Lin; et al. "Characterizing human perceptual inefficiencies with equivalent internal noise." JOSA A 16.3 (1999): 764-778.
Watson, Andrew B.; et al. "Quest: A Bayesian adaptive psychometric method." Perception & psychophysics 33.2 (1983): 113-120.
Green, David Marvin; et al. Signal detection theory and psychophysics. Vol. 1. New York: Wiley, 1966.
Marc, Robert E., et al. "Neural remodeling in retinal degeneration." Progress in retinal and eye research 22.5 (2003) 507-655.
Stasheff, Steven F.; et al. "Developmental time course distinguishes changes in spontaneous and light-evoked retinal ganglion cell activity in rd1 and rd10 mice." Journal of neurophysiology 105.6 (2011): 3002-3009.
Pardhan, S., et al. "A comparison of sampling efficiency and internal noise level in young and old subjects." Vision research 36.11 (1996): 1641-1648.
Bennett, Patrick J.; et al. "Effects of aging on calculation efficiency and equivalent noise." JOSA A 16.3 (1999) 654-668.
Davis, Matthew D., et al. "Risk factors for high-risk proliferative diabetic retinopathy and severe visual loss: Early Treatment Diabetic Retinopathy Study Report# 18." Investigative ophthalmology & visual science 39.2 (1998) 233-252.
Wilkinson, C. P., et al. "Proposed international clinical diabetic retinopathy and diabetic macular edema disease severity scales." Ophthalmology 110.9 (2003): 1677-1682.
Della Sala, S., et al. "Impaired contrast sensitivity in diabetic patients with and without retinopathy: a new technique for rapid assessment." British journal of ophthalmology 69 2 (1985): 136-142.
Di Leo, Mauro AS, et al. "Nonselective loss of contrast sensitivity in visual system testing in early type I diabetes." Diabetes care 15.5 (1992): 620-625.
Ghafour, I. M., et al. "Contrast sensitivity in diabetic subjects with and without retinopathy." The British journal of ophthalmology 66.8 (1982): 492.
Gualtieri, Mirella, et al. "Contrast sensitivity mediated by inferred magno-and parvocellular pathways in type 2 diabetics with and without nonproliferative retinopathy." Investigative Ophthalmology & Visual Science 52.2 (2011): 1151-1155.
Howes, Sharon C.; et al. "Contrast sensitivity in diabetics with retinopathy and cataract." Australian Journal of Opthalmology 10.3 (1982): 173-178.
Leonova, Anna; et al. "Spatial frequency processing in inferred PC-and MC-pathways." Vision Research 43.20 (2003): 2133-2139.
McAnany, J. Jason; et al. "Spatial frequencies used in Landolt C orientation judgments: relation to inferred magnocellular and parvocellular pathways." Vision research 48.26 (2008): 2615-2624.
Pokorny, Joel. "Steady and pulsed pedestals, the how and why of post-receptoral pathway separation." Journal of Vision 11.5 (2011): 7-7.
Pokorny, Joel; et al. "Psychophysical signatures associated with magnocellular and parvocellular pathway contrast gain." JOSA A 14.9 (1997): 2477-2486.

(56) References Cited

OTHER PUBLICATIONS

Montesano, G., et al. "Structure-function relationship in early diabetic retinopathy: a spatial correlation analysis with OCT and microperimetry." Eye 31.6 (2017): 931-939.
Hall, Cierra M.; et al. "Luminance noise as a novel approach for measuring contrast sensitivity within the magnocellular and parvocellular pathways" Journal of Vision 17.8 (2017): 5-5.
Hall, Cierra; et al. "Individual letter contrast thresholds: effect of object frequency and noise." Optometry and vision science: official publication of the American Academy of Optometry 92.12 (2015): 1125.
Garcia-Perez, Miguel A. "Forced-choice staircases with fixed step sizes: asymptotic and small-sample properties." Vision research 38.12 (1998): 1861-1881.
Gastinger, Matthew J., et al. "Dendrite remodeling and other abnormalities in the retinal ganglion cells of Ins2Akita diabetic mice." Investigative ophthalmology & visual science 49.6 (2008): 2635-2642.
Anastasakis, Anastasios, et al. "Clinical value, normative retinal sensitivity values, and intrasession repeatability using a combined spectral domain optical coherence tomography/scanning laser ophthalmoscope microperimeter." Eye 25.2 (2011): 245-251.
Van Dijk, Hille W., et al. "Selective loss of inner retinal layer thickness in type 1 diabetic patients with minimal diabetic retinopathy." Investigative ophthalmology & visual science 50.7 (2009): 3404-3409.
Van Dijk, Hille W., et al. "Decreased retinal ganglion cell layer thickness in patients with type 1 diabetes." Investigative ophthalmology & visual science 51.7 (2010): 3660-3665.
Van Dijk, Hille W., et al. "Early neurodegeneration in the retina of type 2 diabetic patients." Investigative ophthalmology & visual science 53.6 (2012): 2715-2719.
Pelli, Denis G., et al. "Feature detection and letter identification." Vision research 46.28 (2006): 4646-4674.
Gastinger, Matthew J.; et al. "Loss of cholinergic and dopaminergic amacrine cells in streptozotocin-diabetic rat and Ins2Akita-diabetic mouse retinas" Investigative ophthalmology & visual science 47.7 (2006): 3143-3150.
Elsner, A. E., et al. "Cone photopigment bleaching abnormalities in diabetes." Investigative ophthalmology & visual science 28.4 (1987): 718-724.
Forooghian, Farzin, et al. "Relationship between photoreceptor outer segment length and visual acuity in diabetic macular edema." Retina (Philadelphia, Pa.) 30.1 (2010): 63.
Holopigian, Karen, et al. "Evidence for photoreceptor changes in patients with diabetic retinopathy." Investigative ophthalmology & visual science 38.11 (1997): 2355-2365.
Bogdanov, Patricia, et al. "The db/db mouse: a useful model for the study of diabetic retinal neurodegeneration." PLOS one 9.5 (2014): e97302.
Park, S-H., et al. "Apoptotic death of photoreceptors in the streptozotocin-induced diabetic rat retina." Diabetologia 46.9 (2003): 1260-1268.
Baldwin, Alex S., Daniel H. Baker, and Robert F. Hess. "What do contrast threshold equivalent noise studies actually measure? Noise vs. nonlinearity in different masking paradigms." PloS one 11.3 (2016): e0150942.
Fishman, Gerald A. "Retinitis pigmentosa: visual loss." Archives of Ophthalmology 96.7 (1978): 1185-1188.
Marmor, Michael F. "Visual loss in retinitis pigmentosa." American journal of ophthalmology 89.5 (1980): 692-698.
Sues, F. E. "Alteration of the light thresholds in scotopic and photopic vision in retinitis pigmentosa." Ophthalmic paediatrics and genetics 4.3 (1984): 171-176.
Kersten, D., R. F. Hess, and G. T. Plant. "Assessing contrast sensitivity behind cloudy media." Clinical Vision Sciences 2.3 (1988): 143-158.
Pardhan, S. H. A. H. I. N. A., J. Gilchrist, and Guan Khar Beh. "Contrast detection in noise: a new method for assessing the visual function in cataract." Optometry and vision science: official publication of the American Academy of Optometry 70.11 (1993): 914-922.
Kobrin Klein, Barbara Eden. "Overview of epidemiologic studies of diabetic retinopathy." Ophthalmic epidemiology 14.4 (2007): 179-183.
Banford, D., et al. "Longitudinal study of visual functions in young insulin dependent diabetics." Ophthalmic and Physiological Optics 14 4 (1994): 339-346.
Hyvärinen, Lea, Pentti Laurinen, and Jyrki Rovamo. "Contrast sensitivity in evaluation of visual impairment due to diabetes." Acta ophthalmologica 61.1 (1983): 94-101.
Pardhan, Shahina. "Contrast sensitivity loss with aging: sampling efficiency and equivalent noise at different spatial frequencies." JOSA A 21.2 (2004): 169-175.
National Research Council. Recommended standard procedures for the clinical measurement and specification of visual acuity. S. Karger, 1980.
Chen, Ge, et al. "Noise provides new insights on contrast sensitivity function." PloS one 9.3 (2014): e90579.

\* cited by examiner

FIG. 1
(PRIOR ART)

171 — PRESENTING TO A SUBJECT A SERIES OF SCENES, EACH SCENE COMPRISING A FIRST TARGET HAVING A RESPECTIVE LEVEL OF CONTRAST SUPERIMPOSED ON A UNIFORM GRAY FIELD BACKGROUND AND A SECOND TARGET HAVING A RESPECTIVE LEVEL OF CONTRAST SUPERIMPOSED ON A LUMINANCE NOISE BACKGROUND, WHEREIN IN EACH SUCCESSIVELY PRESENTED SCENE, THE FIRST AND SECCOND TARGETS SUPERIMPOSED ON THE UNIFORM GRAY FIELD BACKGROUND AND ON THE LUMINANCE NOISE BACKGROUND, RESPECTIVELY, HAVE RESPECTIVE CONTRAST LEVELS THAT ARE DIFFERENT FROM THE RESPECTIVE CONTRAST LEVELS OF THE FIRST AND SECOND TARGETS, RESPECTIVELY, IN THE PRECEDING SCENE

172 — MONITOR THE SUBJECT'S RESPONSES TO THE PRESENTED SERIES OF SCENES

173 — EVALUATE CONTRAST SENSITIVITY OF THE SUBJECT BASED AT LEAST IN PART ON THE MONITORED RESPONSES

FIG. 4

METHODS AND DIAGNOSTIC TOOLS FOR MEASURING VISUAL NOISE-BASED CONTRAST SENSITIVITY

CROSS-REFERENCE TO RELATED APPLICATIONS

The present application is a national stage entry pursuant to 35 U.S.C. § 371 of International Application No. PCT/2018/062798, filed on Nov. 28, 2018, which claims the benefit of and priority to U.S. Provisional Application No. 62/593,306, filed on Dec. 1, 2017 and entitled "METHODS AND DIAGNOSTIC TOOLS FOR MEASURING VISUAL NOISE BASED CONTRAST SENSITIVITY", which are hereby incorporated by reference herein in their entireties.

BACKGROUND

Contrast sensitivity (CS), the ability to perceive differences in light, is a fundamental function of the visual system that is highly associated with the ability to perform tasks of daily living. Although visual acuity is the most common measure of visual function, some ocular diseases result in CS losses without affecting visual acuity. FIG. 1 shows a Pelli-Robson CS chart, which is the most common diagnostic tool used to measure CS in the clinic. On this chart, the letters become more faint (lower contrast) from left to right, top to bottom; the lowest contrast letter that can be correctly identified provides a measure of the patient's CS.

Although the chart is useful, it has several known limitations that have been discussed in the literature. For example, the large size of the chart renders it difficult to illuminate evenly and results in limited portability; it has low sensitivity for some ocular diseases; and it cannot differentiate among possible causes of CS abnormality.

Thus, there is a need for novel approaches for CS measurement that overcome known limitations of conventional CS tests.

Recently, computer-based CS measurements have been performed in the presence of white luminance noise as a means to overcome existing limitations, enhance test sensitivity, and better enable disease detection. Noise-based measurements have been shown to identify dysfunction in patients with retinitis pigmentosa, who have normal CS as assessed by conventional testing. Similar results have been obtained in patients with early-stage diabetic retinopathy. However, these prior results were obtained using custom computer-implemented CS in noise paradigms that require specialized hardware and software. Due to limited hardware and software availability, this approach cannot be easily expanded or scaled for general clinical use.

Currently, there is no commercially available test of CS in visual luminance noise.

FIG. 2 shows a chart known as the Pelli-Levi Dual Acuity chart. The noise-based CS chart in accordance with the inventive principles and concepts differs from the Pelli-Levi Dual Acuity Chart in that the Pelli-Levi Dual Acuity chart measures visual acuity (the ability to identify small letters) in the presence and absence of noise, whereas the noise-based CS chart measures CS (the ability to identify faint letters) in the presence and absence or noise. It is not possible to measure CS in the presence and absence of noise with the Pelli-Levi Dual Acuity chart.

FIG. 3 shows a chart known as the Pelli Letters-in-Noise chart. The noise-based CS chart in accordance with the inventive principles and concepts differs from the Pelli Letters-in-Noise chart in that the Pelli Letters-in-Noise chart measures the amount of noise needed to reduce letter visibility (i.e., the noise level is manipulated), whereas the noise-based CS chart measures CS in the presence of one constant level of noise and in the absence of noise and compares the difference. It is not possible to measure CS in the presence and absence of noise with the Pelli Letters-in-Noise chart.

SUMMARY

The present disclosure provides a method and a diagnostic tool for assessing contrast sensitivity in a subject. In accordance with an embodiment, the method comprises:

i) presenting to a subject a series of scenes, each scene comprising at least a first target having a preselected level of contrast superimposed on a uniform background and a second target having a preselected level of contrast superimposed on a luminance noise background, wherein in each successively presented scene the first and second targets that are superimposed on the uniform background and on the luminance noise background, respectively, have contrast levels that are different from the contrast levels of the first and second targets superimposed on the uniform background and on the luminance noise background, respectively, in the previously presented scene;

ii) monitoring responses by the subject to step i); and iii) evaluating the contrast sensitivity of the subject based on the monitored responses.

In accordance with an embodiment of the method, the uniform background is a uniform gray field background.

In accordance with an embodiment of the method, the luminance noise background has a substantially constant level of luminance noise over the series of scenes.

In accordance with an embodiment of the method, the preselected level of contrast of the first target of each scene ranges from 58 percent to 0.5 percent over the series.

In accordance with an embodiment of the method, the preselected level of contrast of the second target of each scene ranges from 58 percent to 0.5 percent over the series.

In accordance with an embodiment of the method, in at least a first scene of the series, the preselected level of contrast of the first target and the preselected level of contrast of the second target are equal to a first level of contrast.

In accordance with an embodiment of the method, in at least a second scene of the series that is presented to the subject in immediate succession to the first scene being presented to the subject, the preselected level of contrast of the first target and the preselected level of contrast of the second target are equal to a second level of contrast.

In accordance with an embodiment of the method, the second level of contrast is less than the first level of contrast.

In accordance with an embodiment of the method, the second level of contrast is greater than the first level of contrast.

In accordance with an embodiment of the method, step i) is performed by a computer system having one or more processors that perform one or more algorithms to cause the series of scenes to be displayed on a display monitor of the computer system.

In accordance with an embodiment of the method, step ii) is performed by the computer system by receiving as input selections made by the subject on an input device of the computer system, the selections corresponding to the responses.

In accordance with an embodiment of the method, step iii) is performed by the one or more processors performing one or more algorithms that process the received input to evaluate the contrast sensitivity of the subject based on the received input.

In accordance with an embodiment of the method, step iii) includes determining whether the contrast sensitivity of the subject is normal or abnormal in the presence of luminance noise and whether the contrast sensitivity of the subject is normal or abnormal in the absence of luminance noise.

In accordance with an embodiment of the method, the determination is indicative of whether the subject has a disease selected from the group including amblyopia, juvenile x-linked retinoschisis, moderate-late stage glaucoma, retinitis pigmentosa, diabetic retinopathy and early glaucoma.

In accordance with an embodiment of the method, the successive scenes are presented sequentially in book fashion on successive pages.

In accordance with an embodiment of the method, the successive scenes are presented as images adjacent to one another on a single page or chart.

In accordance with an embodiment of the diagnostic tool, the tool comprises: a series of scenes to be presented to the subject, each scene comprising at least a first target having a preselected level of contrast superimposed on a uniform background and a second target having a preselected level of contrast superimposed on a luminance noise background, wherein in each successively presented scene the first and second targets that are superimposed on the uniform background and on the luminance noise background, respectively, have contrast levels that are different from the contrast levels of the first and second targets superimposed on the uniform background and on the luminance noise background, respectively, in the previously presented scene.

In accordance with an embodiment of the diagnostic tool, the diagnostic tool comprises a book having a cover and a plurality of pages arranged within the cover, each page having at least one of the scenes disposed thereon.

In accordance with an embodiment of the diagnostic tool, the diagnostic tool comprises at least one sheet or substrate having a plurality of the scenes disposed thereon.

In accordance with an embodiment of the diagnostic tool, the book has a size that is less than or equal to nine inches by seven inches, respectively, and wherein the size of the book makes the scenes generally insensitive to the room lighting conditions.

These and other features and advantages will become apparent from the following description, drawings and claims.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

FIG. 1 shows an example of the Pelli-Robson CS Chart.

FIG. 4 illustrates a flow diagram that represents the method for assessing CS of a subject in accordance with a representative embodiment.

DETAILED DESCRIPTION

Figure 2:
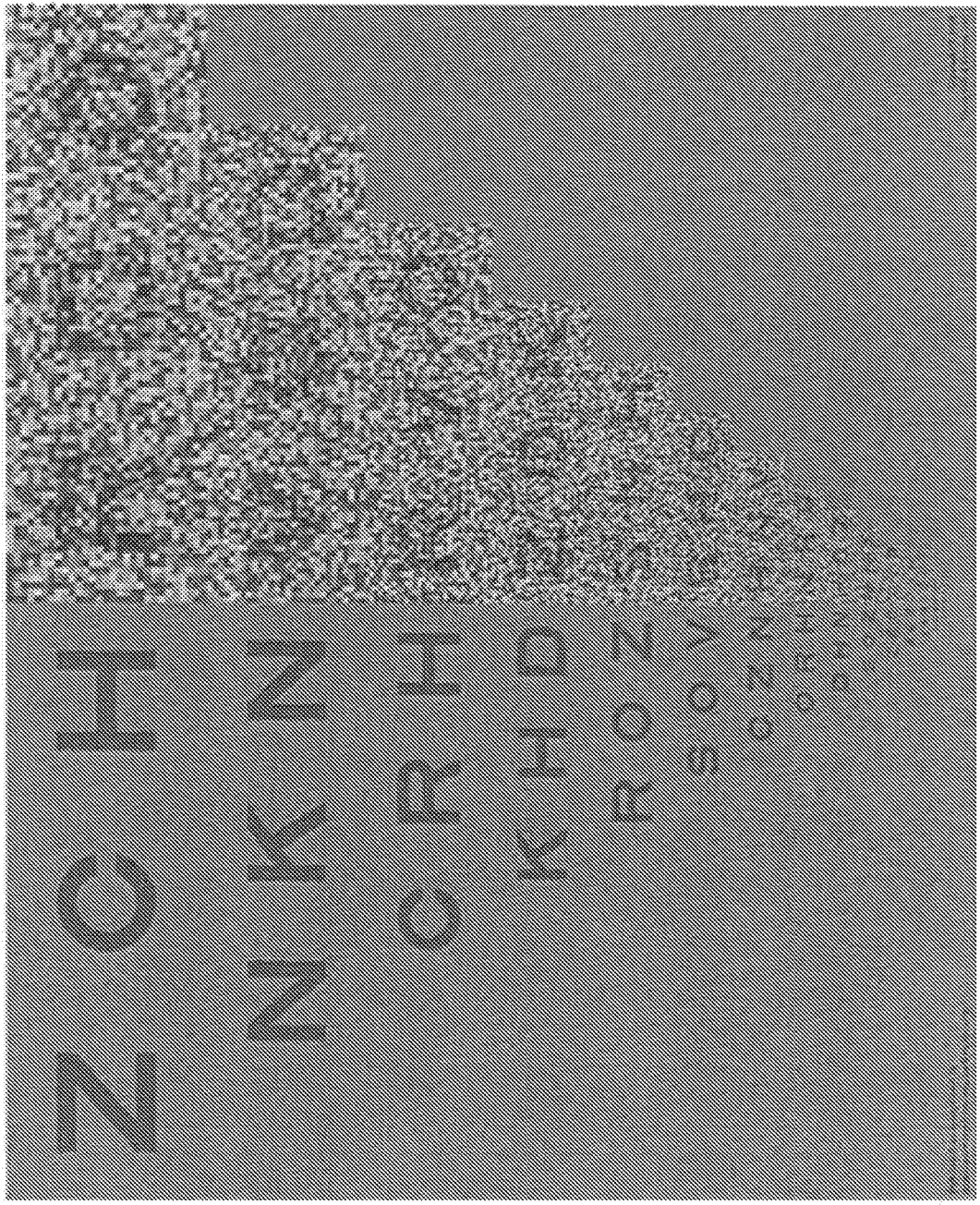
FIG. 2 shows an example of the Pelli-Levi Dual Acuity Chart (letter acuity in noise approach).

The present disclosure is directed to methods and diagnostic tools for assessing CS in a subject in the presence and absence of luminance noise by: i) presenting to a subject a series of scenes, each scene comprising at least a first target having a preselected level of contrast superimposed on a uniform background and a second target having a preselected level of contrast superimposed on a luminance noise background, wherein in each successively presented scene the first and second targets that are superimposed on the uniform background and on the luminance noise background, respectively, have contrast levels that are different from the contrast levels of the first and second targets superimposed on the uniform background and on the luminance noise background, respectively, in the previously presented scene; ii) monitoring responses by the subject to step i); and iii) evaluating the CS of the subject based on the monitored responses.

A few representative embodiments of the diagnostic tool and method will now be described with reference to FIGS. 4-7, in which like reference numerals represent like components, elements or features. It should be noted that features, elements or components in the figures are not intended to be drawn to scale, emphasis being placed instead on demonstrating inventive principles and concepts. It should be noted that the inventive principles and concepts are not limited to the representative embodiments described herein, as will be understood by those of skill in the art in view of the description provided herein.

In the following detailed description, for purposes of explanation and not limitation, exemplary, or representative, embodiments disclosing specific details are set forth in order to provide a thorough understanding of inventive principles and concepts. However, it will be apparent to one of ordinary skill in the art having the benefit of the present disclosure that other embodiments according to the present teachings that are not explicitly described or shown herein are within the scope of the appended claims. Moreover, descriptions of well-known apparatuses and methods may be omitted so as not to obscure the description of the exemplary embodiments. Such methods and apparatuses are clearly within the scope of the present teachings, as will be understood by those of skill in the art. It should also be understood that the word "example," as used herein, is intended to be non-exclusionary and non-limiting in nature.

The terminology used herein is for purposes of describing particular embodiments only, and is not intended to be limiting. The defined terms are in addition to the technical, scientific, or ordinary meanings of the defined terms as commonly understood and accepted in the relevant context.

The terms "a," "an" and "the" include both singular and plural referents, unless the context clearly dictates otherwise. Thus, for example, "a device" includes one device and plural devices. The terms "substantial" or "substantially" mean to within acceptable limits or degrees acceptable to those of skill in the art. The term "approximately" means to within an acceptable limit or amount to one of ordinary skill in the art.

The term "memory" or "memory device", as those terms are used herein, are intended to denote a non-transitory computer-readable storage medium that is capable of storing computer instructions, or computer code, for execution by one or more processors. References herein to "memory" or "memory device" should be interpreted as one or more memories or memory devices. The memory may, for example, be multiple memories within the same computer system. The memory may also be multiple memories distributed amongst multiple computer systems or computing devices.

A "processor," "processing device," or "processing logic," as those terms are used herein, are interchangeable and encompass at least one electronic device that is configured to perform one or more processing algorithms that process signals. The electronic device(s) may perform the algorithm(s) in hardware, software or firmware, or a combination thereof. References herein to a system comprising "a processor" or "a processing device" or "processing logic" should be interpreted as one or more processors or processing cores. The processor may, for instance, be a multi-core processor. A processor may also refer to a collection of processors within a single computer system or distributed amongst multiple computer systems. Instructions of a computer program can be performed by a single processor or by multiple processors that may be within the same device or that may be distributed across multiple devices. The term "controller," as that term is used herein, denotes an electronic device that comprises a processor, a processing device or processing logic, as those terms are defined herein.

As used herein, the term "visual acuity" refers to the smallest target that can be identified at a fixed distance (e.g., sharpness of vision). Reduced visual acuity means that the subject has difficulty seeing objects at a certain distance.

As used herein, the term "luminance" refers to the perceived brightness of a stimulus; the total light reflected from a surface.

As used herein, the term "contrast" refers to the difference between the highest and lowest luminance in a visual display. The contrast of a visual stimulus is the amount of luminance difference between the target (e.g., a letter) and the background.

As used herein, the term "reduced CS" means that the subject cannot identify low luminance (faint) letters at the same performance level as a visually-normal individual. For example, in the Pelli-Robson CS test, the patient begins to make errors on the chart at a level that a visually-normal individual can correctly read (e.g., the patient with CS loss reads fewer letters than normal).

As used herein, the term "target" refers to any character or picture that is presented to the subject for identification. Representative targets include letters, numbers, symbols, or solid representations of items such as animals, faces, common objects or structures, and the like. In a particular embodiment, the target is letters.

As used herein, the term "scene" refers to an image of at least first and second targets superimposed on different backgrounds and presented to a subject for identification, where the first and second targets of each scene have a contrast that is different from the contrast of the first and second targets, respectively, of the previous and succeeding scenes to allow a diagnostic output of a subject's contrast sensitivity to be obtained. The number of scenes that are used to obtain a diagnostic output can be varied.

Known clinical CS charts, which are used to test the ability of a subject to perceive subtle differences in light level, are typically used to determine the faintest target that can be seen by a subject. These tests differ from the ubiquitous visual acuity charts that use black letters of various size on a white background. Laboratory studies show that CS can be reduced in common eye diseases such as glaucoma, diabetic retinopathy, age-related macular degeneration, and cataract. Importantly, CS tests can identify disease in individuals who have normal visual acuity. Furthermore, the FDA has advocated for CS measurement as an outcome measure in clinical trials.

The current standard for measuring CS is the "Pelli-Robson CS chart." Despite its usefulness, however, it suffers from many well-documented limitations, such as relatively poor sensitivity for detecting some eye diseases, inability to distinguish among different diseases, limited portability, and susceptibility to room lighting artifacts. Given these limitations, CS is rarely measured in typical clinical practice.

The diagnostic tools and methods disclosed herein overcome these limitations and disadvantages. In accordance with representative embodiments disclosed herein, a diagnostic tool implemented as a noise-based CS test is used to measures CS in the absence and presence of white luminance noise (e.g., "TV snow"). In accordance with a representative embodiment, the outcome of the test (i.e., normal or abnormal) is based on the following determinations: 1) the total number of targets (e.g., letters) correctly identified in the presence and absence of noise; and 2) the difference in the number of targets correctly identified in the presence and absence of noise. The diagnostic tool in accordance with the inventive principles and concepts comprises a noise-based CS chart that is used during the noise-based CS test to make determinations 1) and 2). The noise-based CS chart provides a novel chart-based metric for detecting eye disease. The noise-based CS chart retains the enhanced sensitivity of computer-implemented noise-based CS tests, as well as the ability to differentiate among diseases, but can be small, portable, quickly administered, and not dependent on room lighting. These attractive features will make CS testing available to a large population of eye care professionals.

In accordance with a representative embodiment of the method, the subject is presented with a noise-based CS chart having a series of targets (e.g., letters) with varying levels of contrast superimposed on a uniform background and a series of different targets with varying levels of contrast presented in luminance noise. The subject is asked to read from left to right and the number of targets that are identified correctly in the presence and absence of noise is recorded. The outcome of the test (i.e., normal or abnormal) preferably is based on aforementioned determinations 1) and 2).

In accordance with another representative embodiment, multiple letters of the same contrast are presented to the subject via the noise-based CS chart together in the presence and absence of luminance noise for multiple chances of success at correctly identifying the letters.

In accordance with another representative embodiment, the noise-based CS chart presents successive letters on separate pages, rather than as a single line or row on the same page.

In accordance with another representative embodiment, multiple letters of the same contrast are presented together on a single page, rather than as a single line or row, in the presence and absence of luminance noise, to allow for multiple chances of success at correctly identifying the letters.

In some embodiments, letters that span a range of contrast (50% to 0.5%) are presented in the chart against a uniform gray field; a different letter of identical contrast is presented via the chart in white luminance noise. In accordance with an embodiment, luminance noise remains constant throughout, whereas the letter contrast decreases from letter to letter in 0.1 log unit steps.

One aspect of the disclosure is directed to a visual noise-based ophthalmic diagnostic tool for assessing letter CS (the ability to identify faint letters against a background) wherein letters at select contrast levels are presented together in the presence and absence of visual luminance (grayscale) noise. Several letters of the same contrast are presented together in the presence and absence of luminance noise for multiple chances of success. Luminance noise remains constant throughout while letter contrast levels decrease on each successive page/line.

Another aspect of this disclosure is a method of assessing CS in a subject comprising: i) presenting to the subject, via the noise-based CS chart, one or more scenes comprising a target having a constant level of contrast superimposed on a uniform gray field and an identical target superimposed on a background having a constant level of white luminance noise; ii) monitoring the subject's responses to step i); and iii) evaluating the CS of the subject based on the responses.

Figure 1:
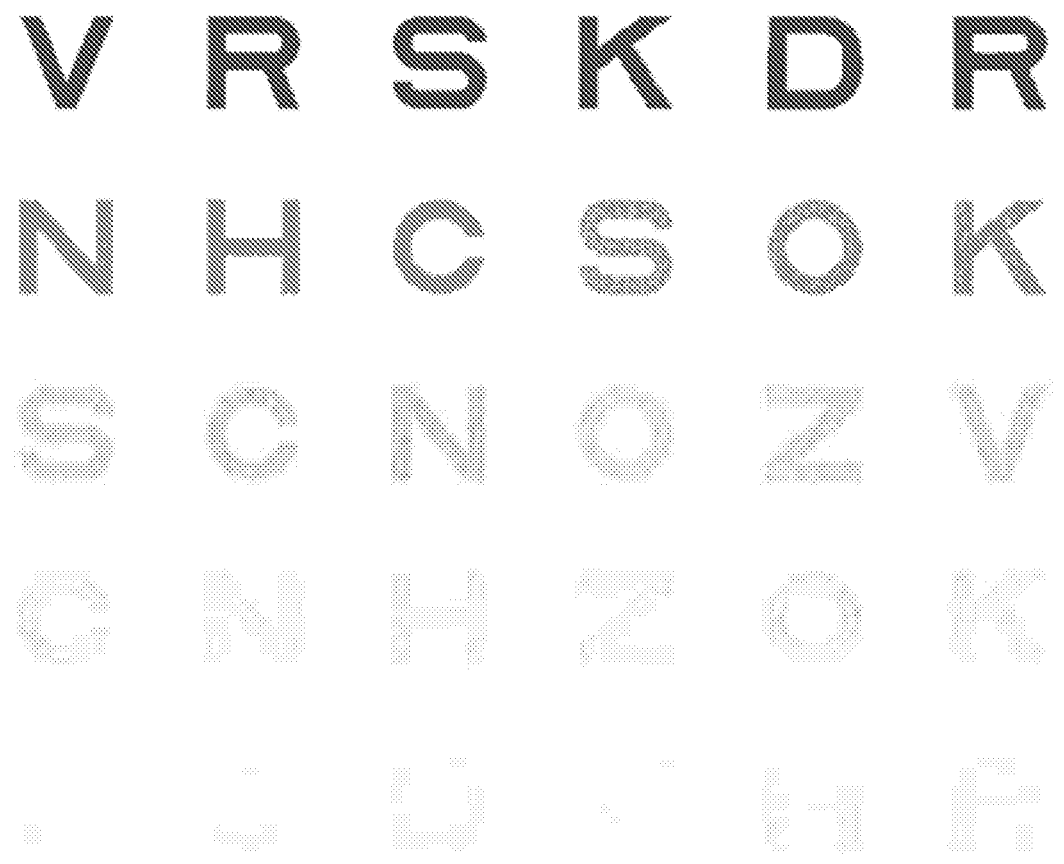
Figure 3:
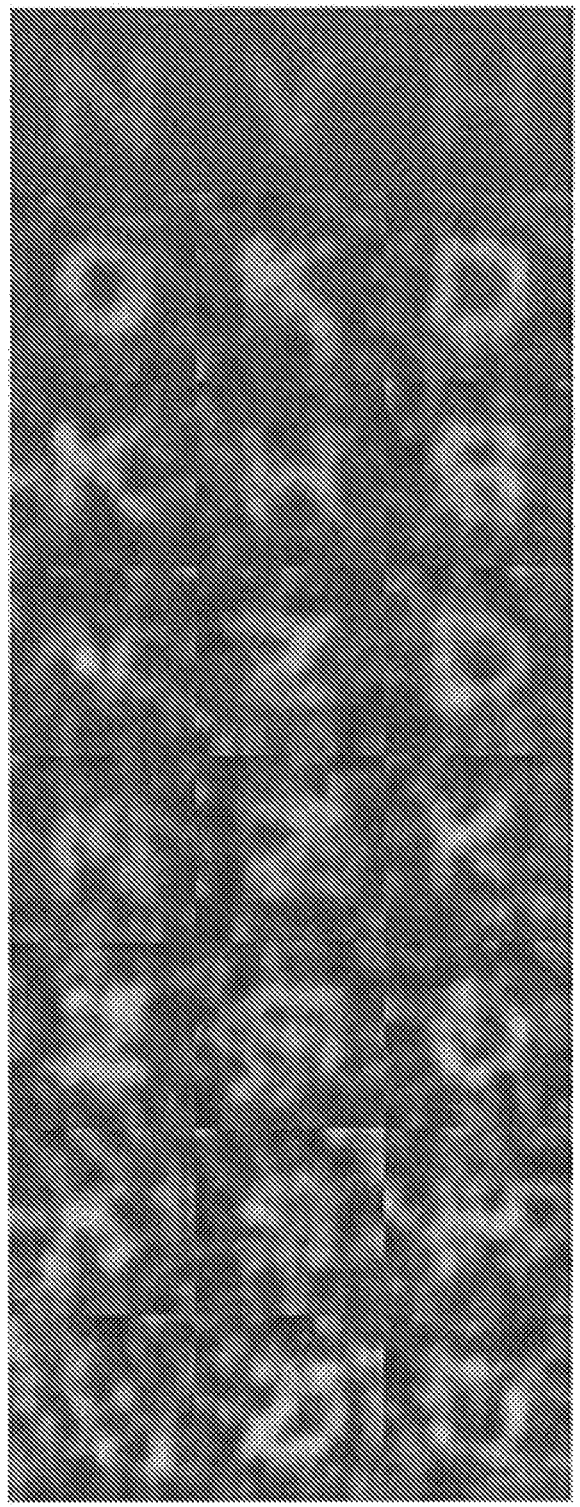
FIG. 3 shows an example of the Pelli Letters-in-Noise Chart (adjust noise level approach).

Compared to currently available ophthalmic diagnostic tools, such as those described above with reference to FIGS. 1-3, the noise-based CS chart in accordance with the present disclosure can be made to be inexpensive, compact, portable, and insensitive to room illumination (i.e., the effects of room illumination are negligible, within reason). The test conducted using the noise-based CS chart disclosed herein is more sensitive than existing testing methodologies and devices.

Studies have been performed by the inventor and others that demonstrate the need for CS measurement in the presence and absence of luminance noise and its importance in evaluating visual dysfunction in patients with retinitis pigmentosa (RP) and diabetic retinopathy (DR). The studies are contained in an article entitled "Reduced Contrast Sensitivity is Associated With Elevated Equivalent Intrinsic Noise in Type 2 Diabetics Who Have Mild or No Retinopathy" by J. Jason McAnany and Jason C. Park, published in Investigative Ophthalmology & Visual Science in April 2018 and in an article entitled "Equivalent Intrinsic Noise, Sampling Efficiency, and Contrast Sensitivity in Patients With Retinitis Pigmentosa" by J. Jason McAnany, Kenneth R. Alexander, Mohamed A. Genead and Gerald A. Fishman, published in Investigative Ophthalmology & Visual Science in May 2013, both of which are hereby incorporated by reference herein in their entireties. The methods and diagnostic tools disclosed herein are intended to fulfill these and other needs, as will be described below with reference to representative embodiments depicted in the drawings.

Figure 5:
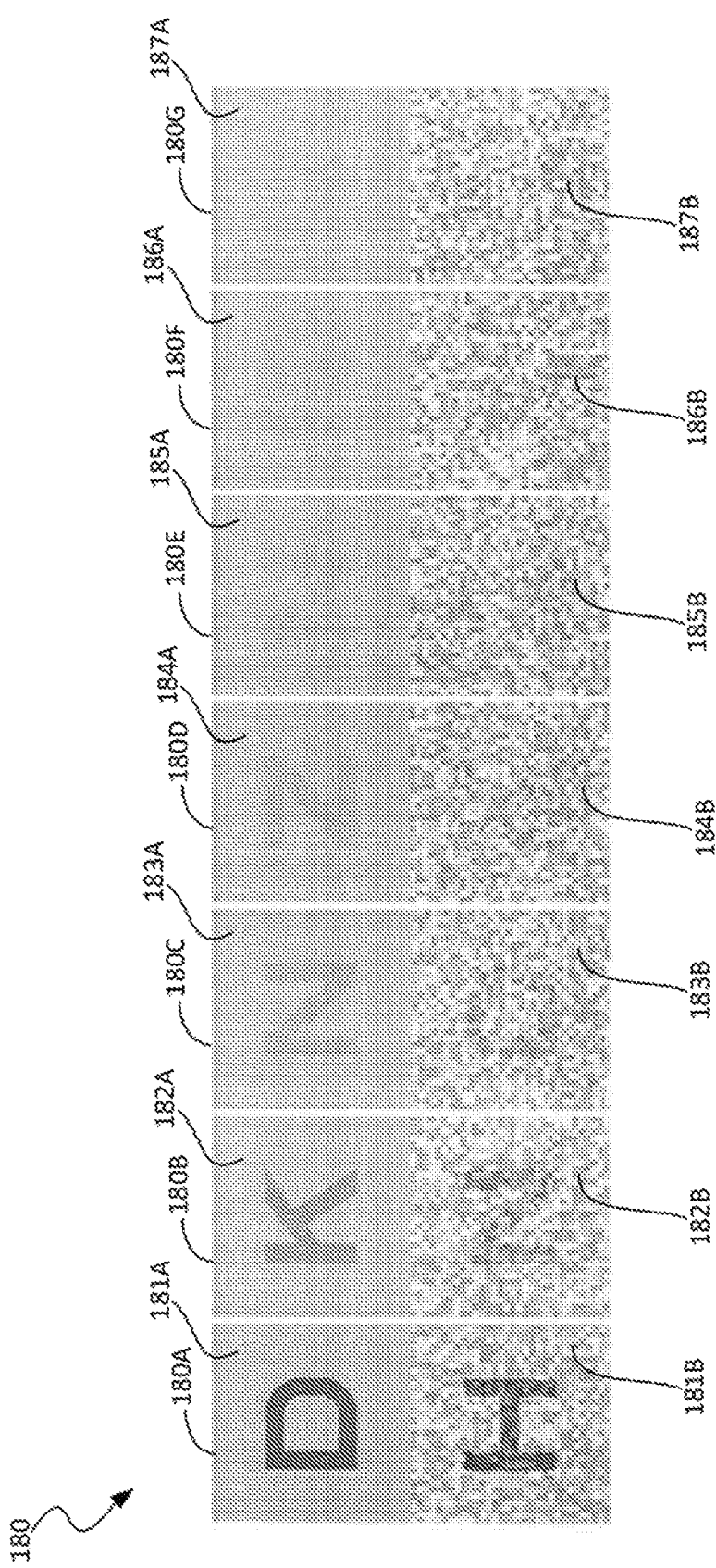
FIG. 5 depicts a test panel comprising a series of scenes of a noise-based CS eye chart in accordance with one representative embodiment.
Figure 6A:
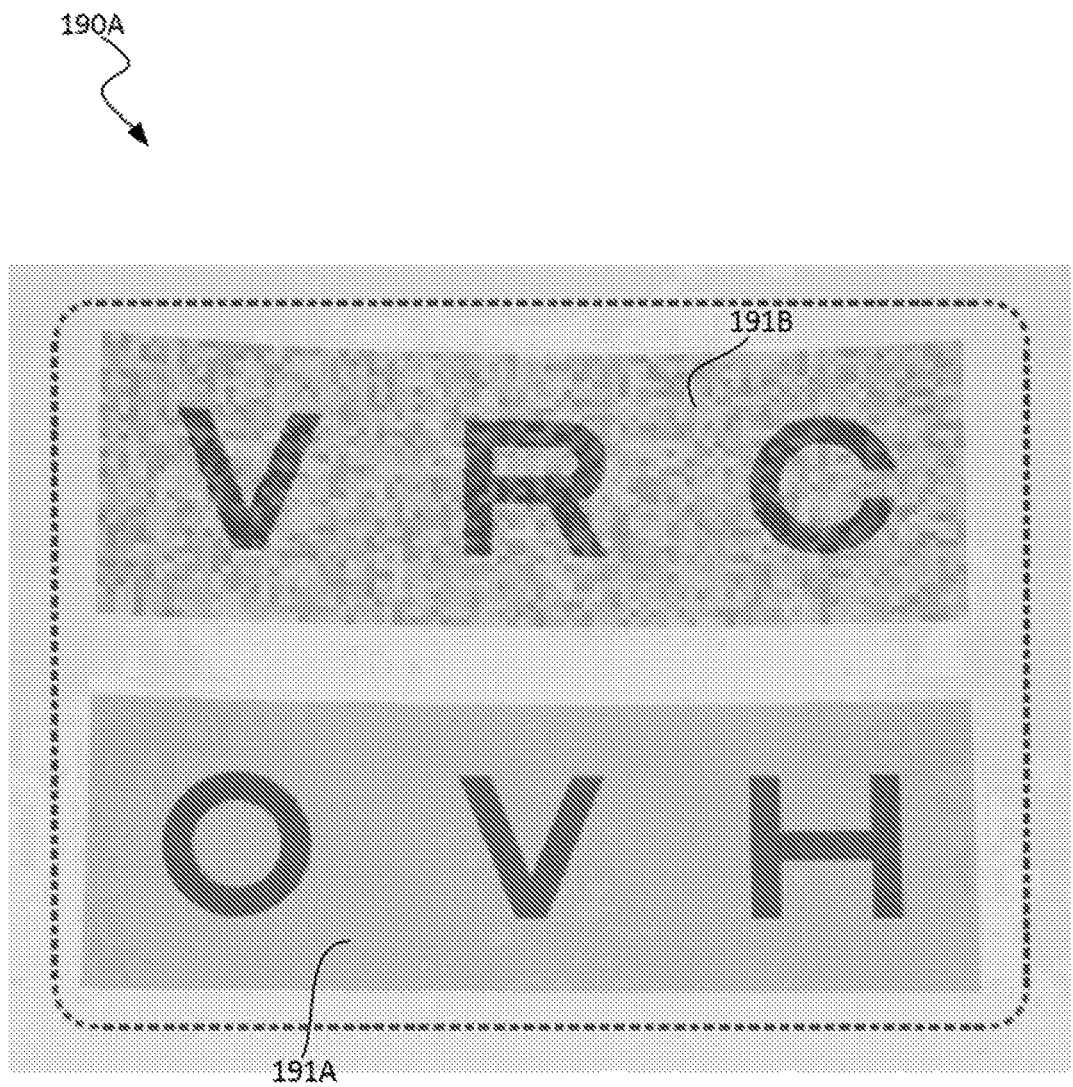
FIGS. 6A-6L depicts scenes displayed on pages of a book or in screen shots on a computer display monitor in accordance with a representative embodiment.

FIG. 4 is a flow diagram representing the method in accordance with a representative embodiment for using a noise-based eye chart to assess CS in a subject. FIGS. 5-6L illustrate the noise-based eye chart in accordance with representative embodiments. The diagnostic tool for displaying the noise-based eye chart may be implemented in a number of ways, including, for example, a book with scenes of the eye chart formed on pages of the book, a single substrate (e.g., a piece of paper) that has the eye chart formed thereon, a computer monitor with the eye chart displayed thereon by a computer that is connected to the display monitor, a hologram, an electronic tablet, a mobile hand-held device such as an iphone or personal digital assistant (PDA), etc. Thus, the diagnostic tool may be a non-electronic device for displaying the eye chart to a subject in printed form or it may be an electronic device or system for displaying the eye chart to a patient in electronic form on a display monitor of the electronic device or system. In the latter case, the diagnostic tool is a computer-implemented apparatus comprising one or more processors configured to perform one or more algorithms that generate the eye chart and cause it to be displayed.

During the step represented by block 171, a subject is presented with a series of scenes, each scene comprising a first target having a respective contrast level superimposed on a uniform background and a second target having a respective contrast level superimposed on a luminance noise background. The term "uniform background," as that term is used herein, means that the corresponding region of the image has a substantially constant average luminance throughout the region. The term "luminance noise background," as that term is used herein, means that the corresponding region of the image has random, or at least pseudorandom, increments and decrements of luminance added to it throughout the region. Persons of skill in the art of visual diagnostic tools will understand the manner in which such backgrounds can be generated.

In each successively presented scene, the first and second targets that are superimposed on the uniform background and on the luminance noise background, respectively, have contrast levels that are different from the contrast levels of the first and second targets superimposed on the uniform background and on the luminance noise background, respectively, in the immediately preceding scene. In accordance with a representative embodiment, the luminance noise background has a substantially constant level of luminance noise over the entire series of scenes presented to the subject. In accordance with a representative embodiment, the uniform background is a uniform gray field background.

Figure 6B:
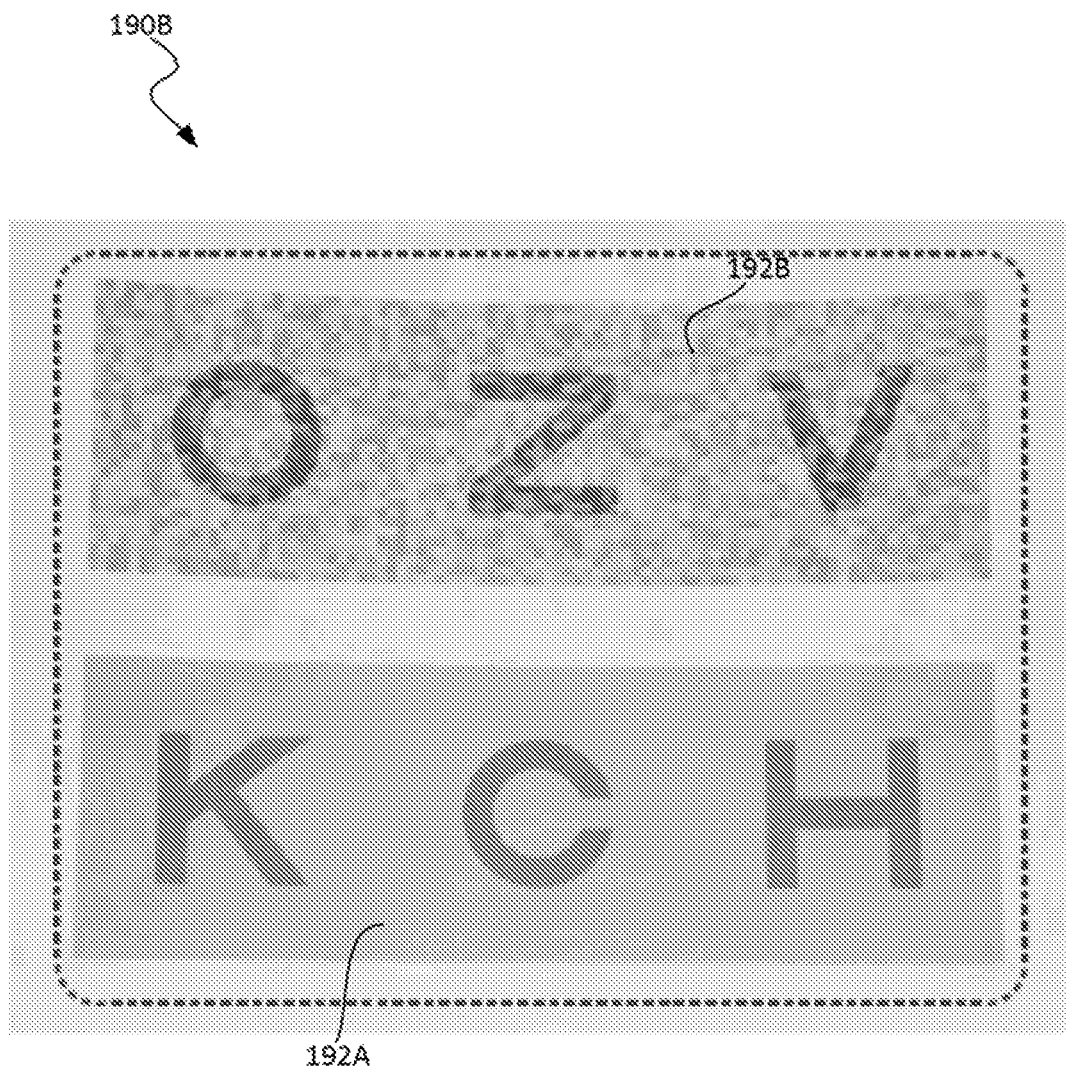
Figure 6C:
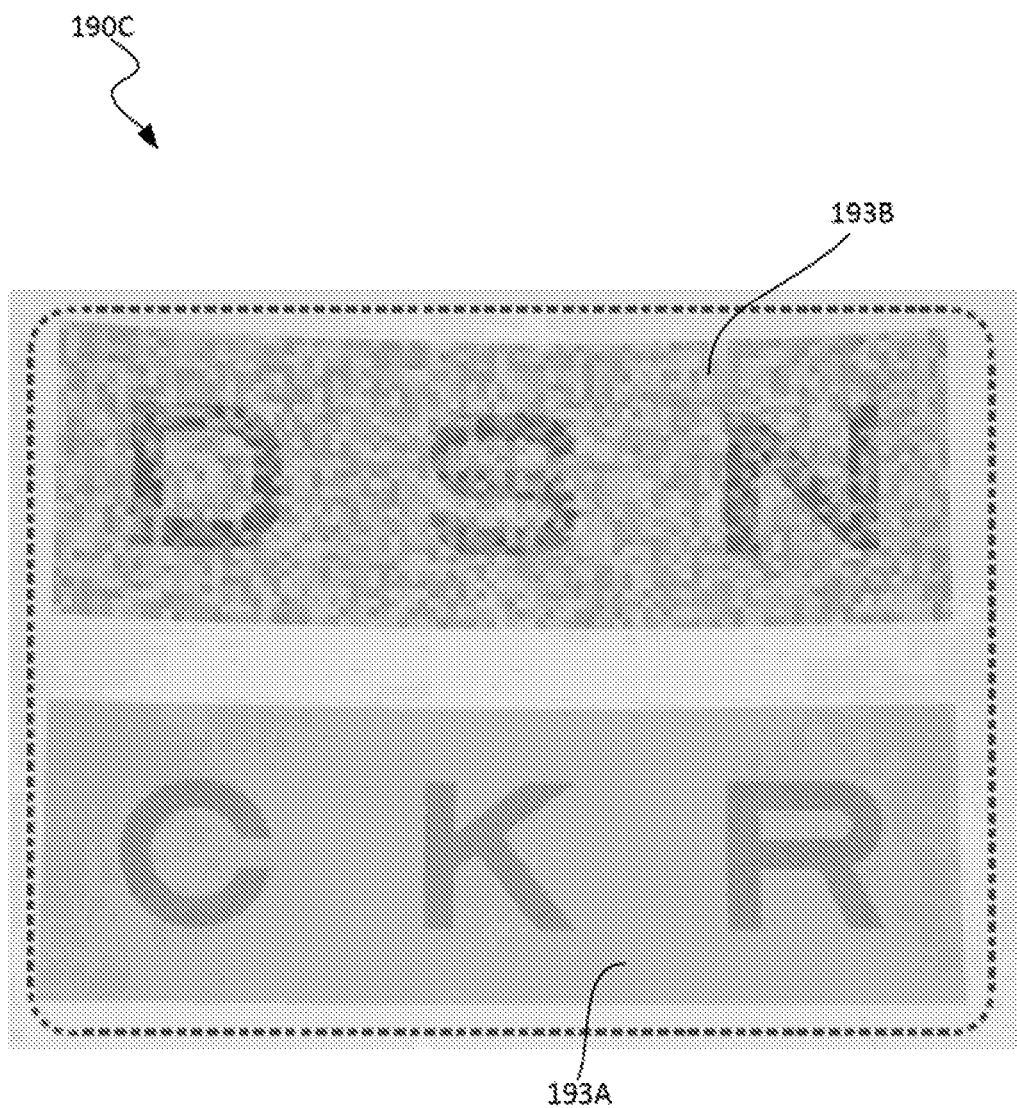
Figure 6D:
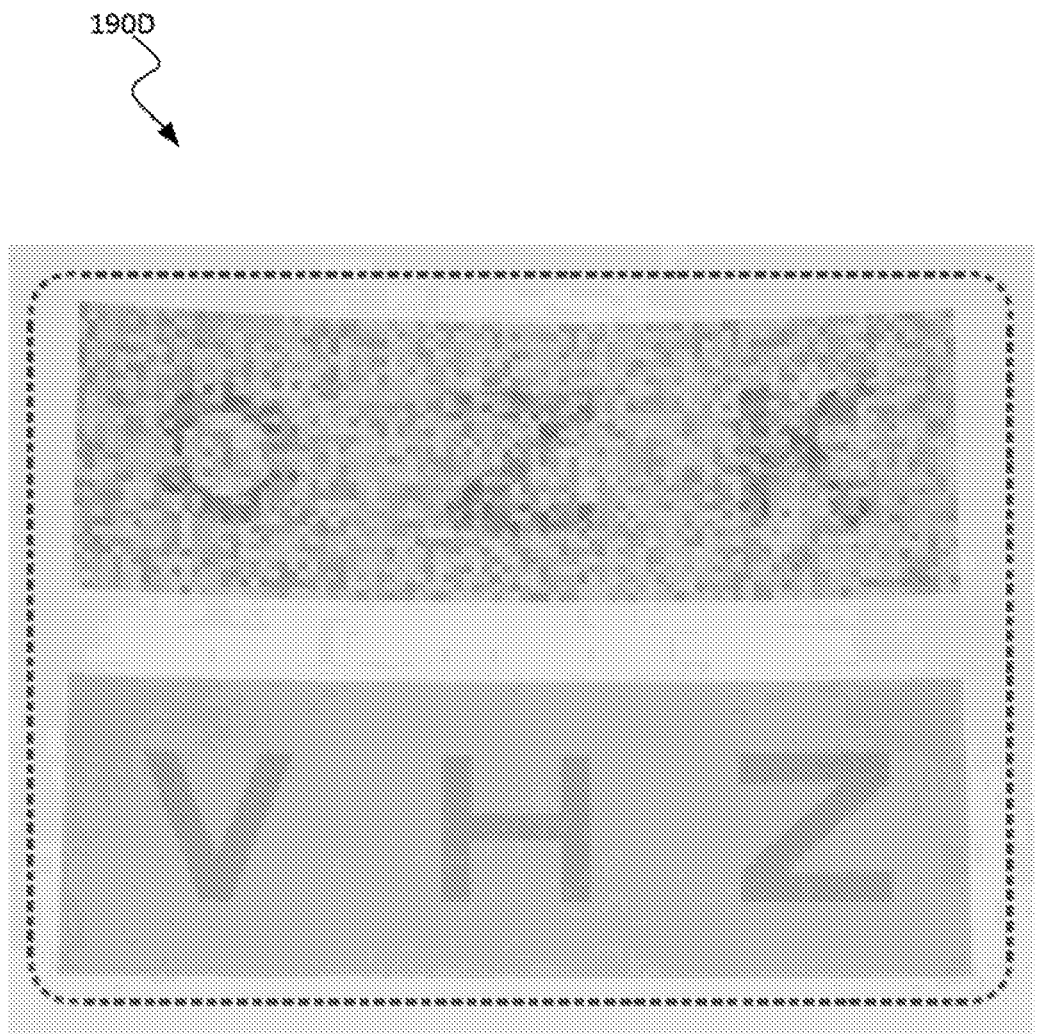
Figure 6E:
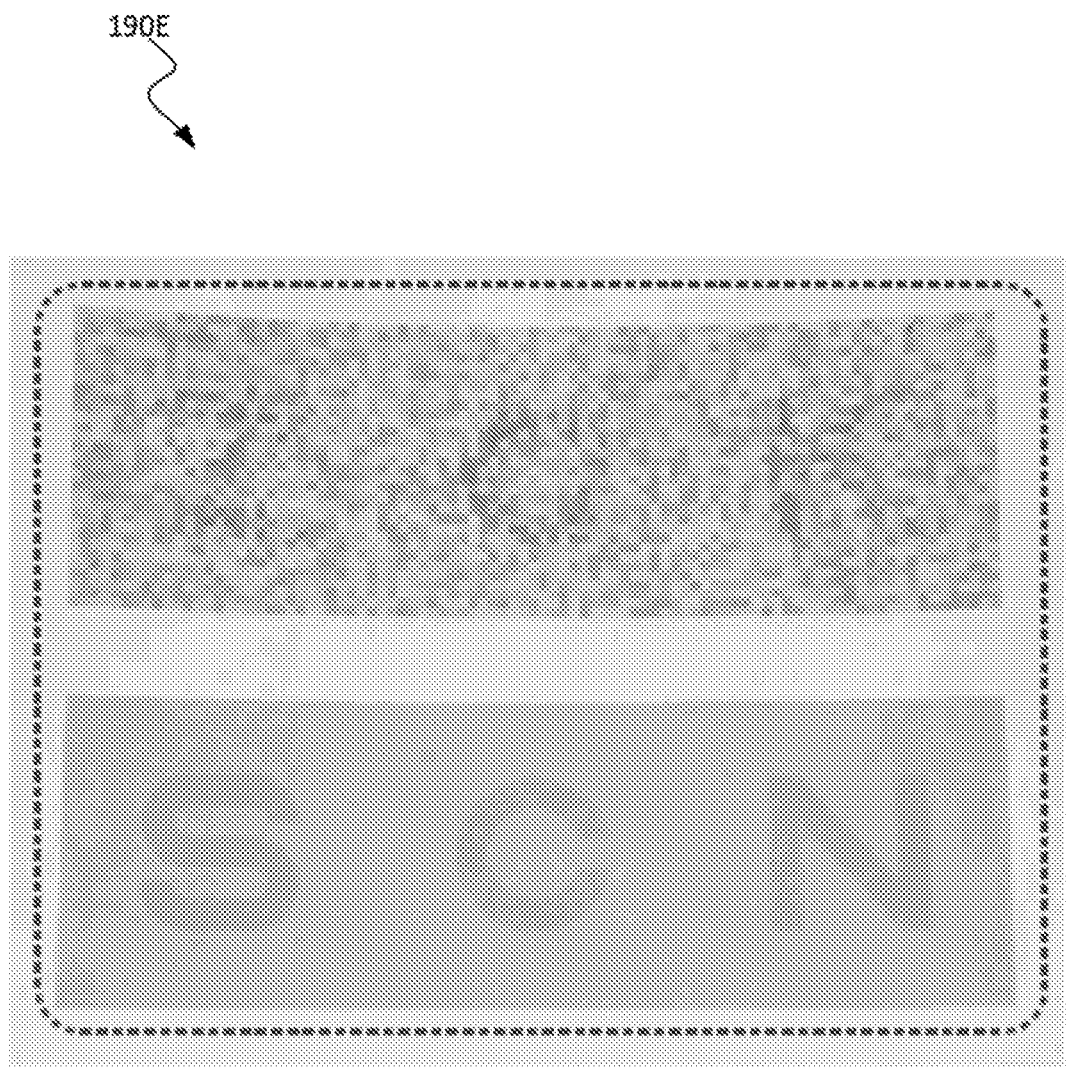
Figure 6F:
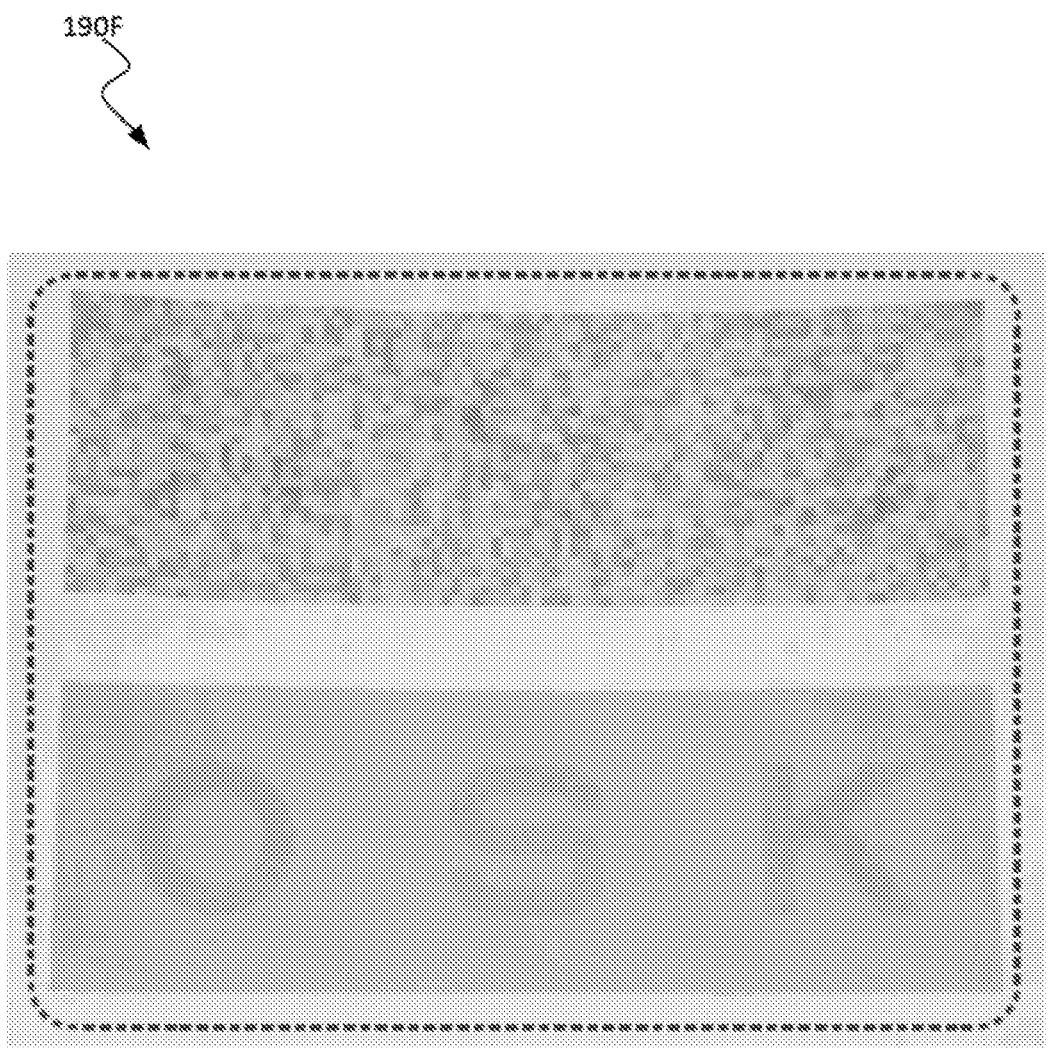
Figure 6G:
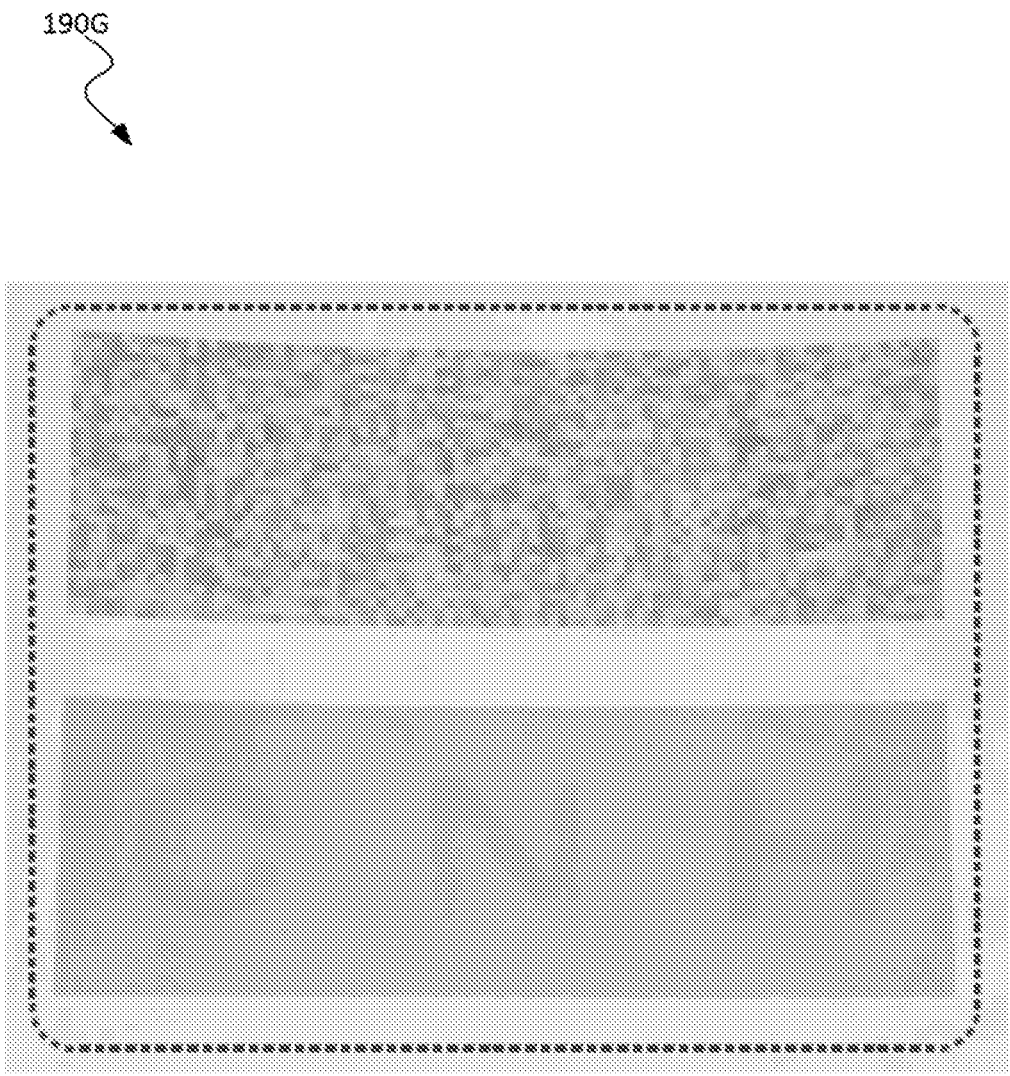
Figure 6H:
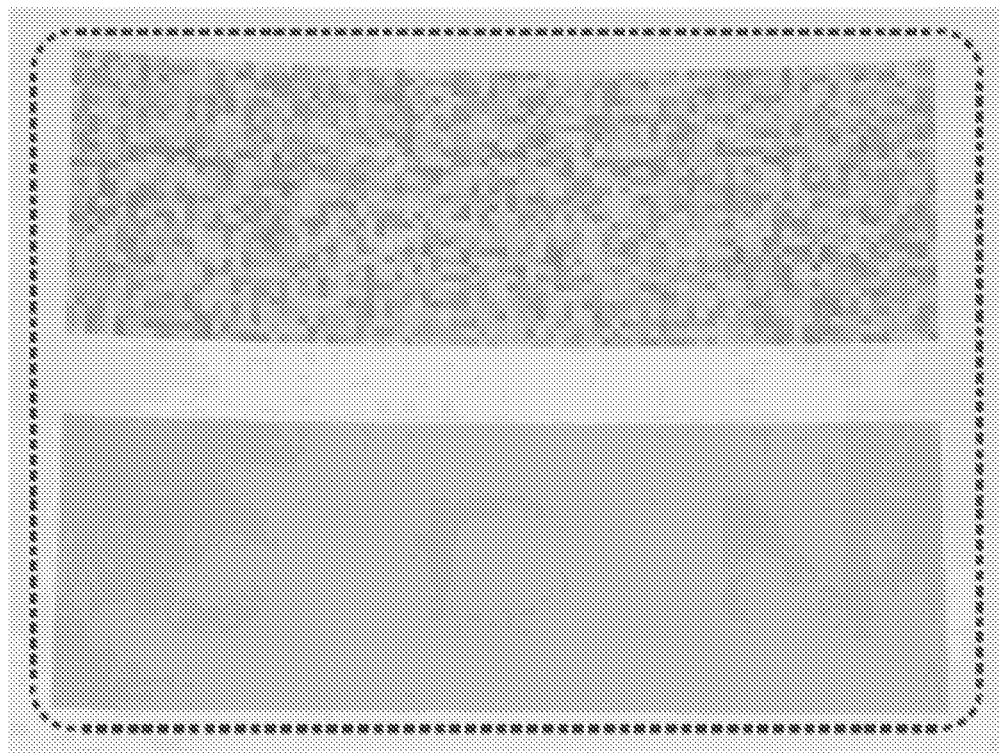
Figure 6I:
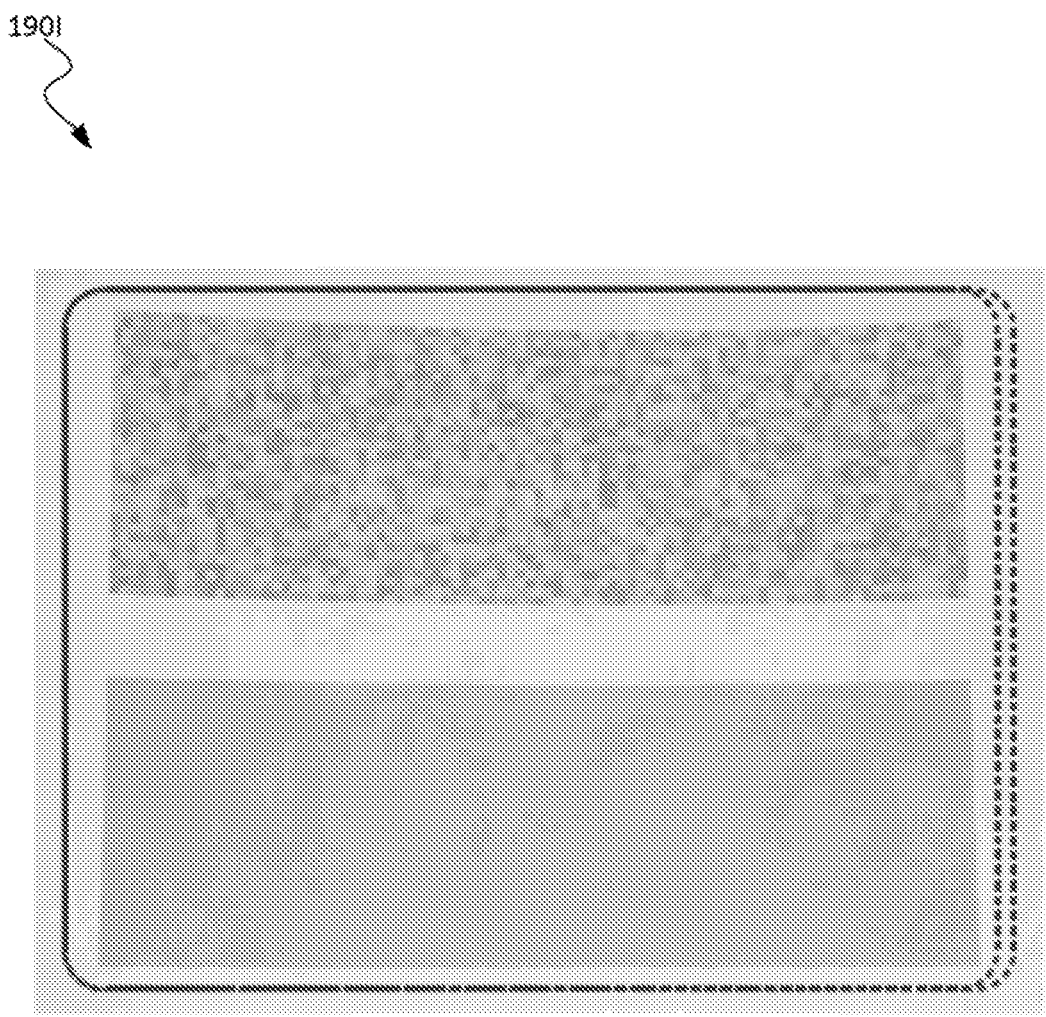
Figure 6J:
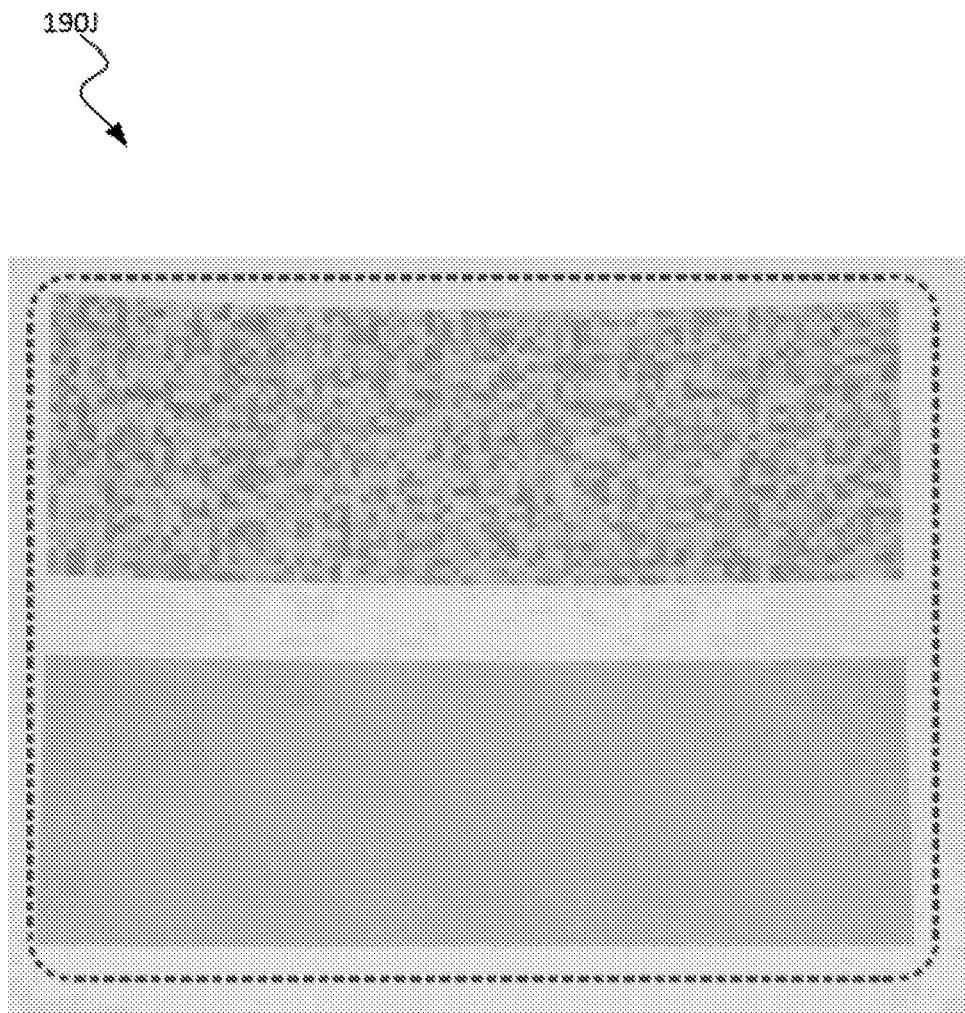
Figure 6K:
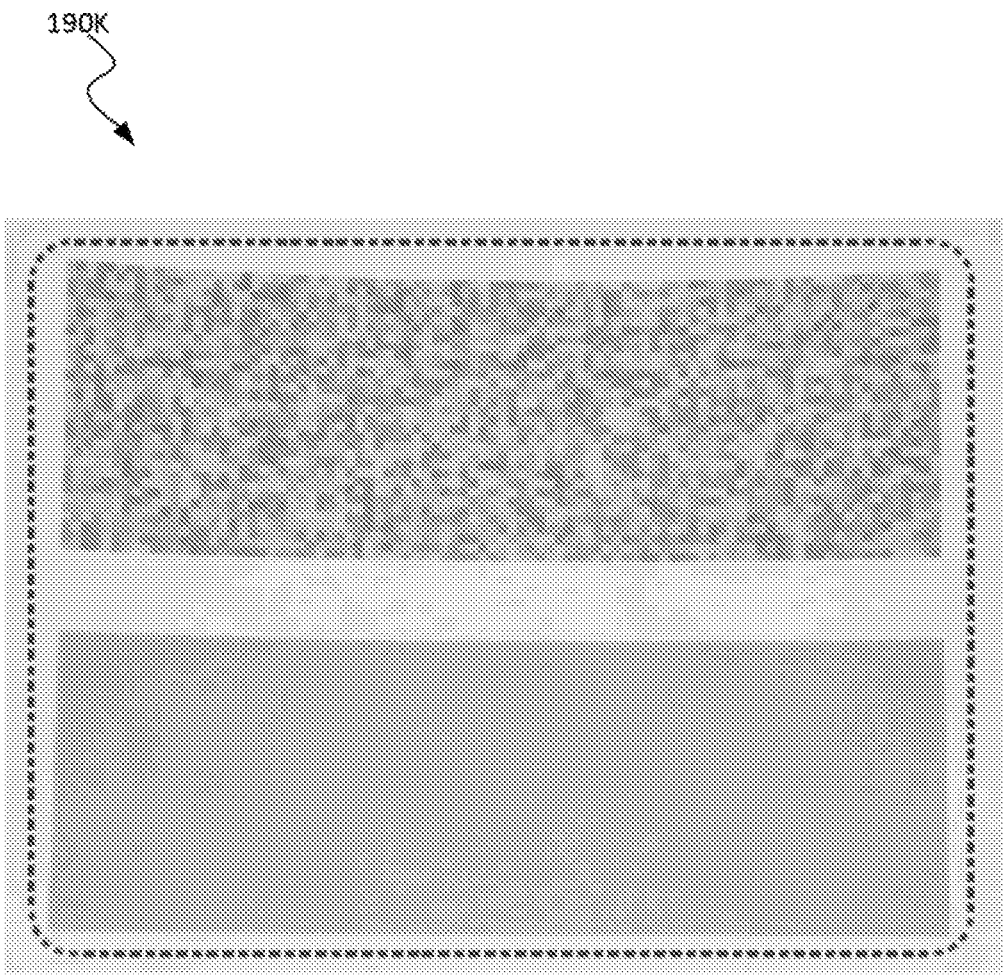
Figure 6L:
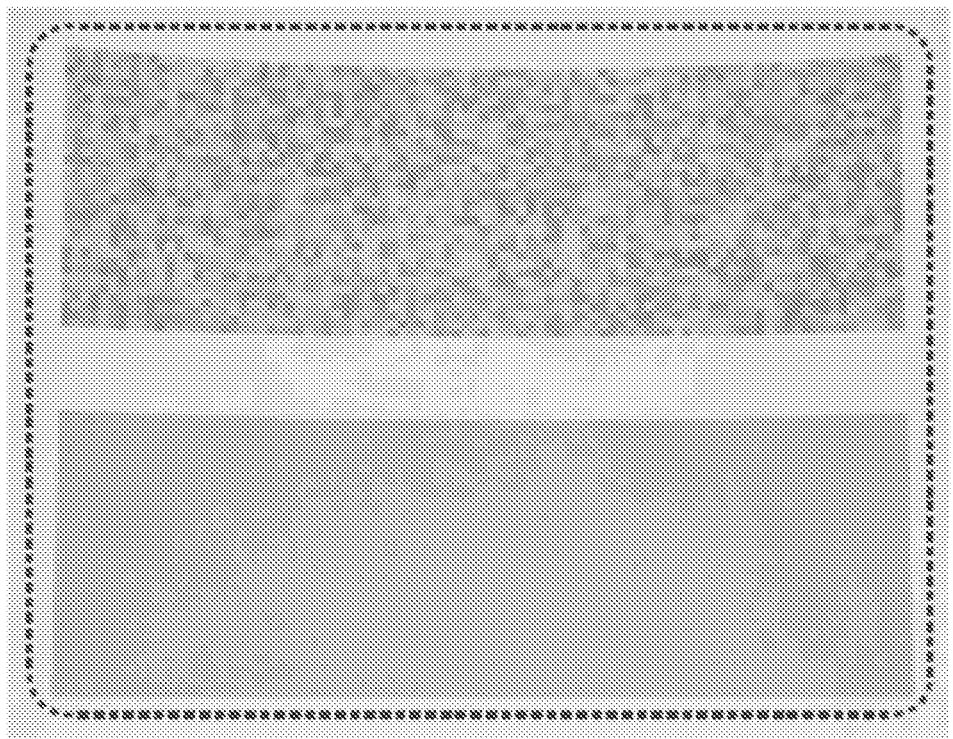

An example of the step represented by block 171 will now be provided with reference to examples of the noise-based eye chart shown in FIGS. 5-6B. FIG. 5 shows the noise-based eye chart 180 in accordance with a representative embodiment in which a series of seven scenes 180A-180G are arranged side-by-side on a page of a book or in a screen shot on a computer display monitor, depending on the manner in which the eye chart 180 is implemented. The first scene 180A in the series has a first target, which in this example is the letter "D," superimposed on a uniform gray field background 181A, and has a second target, which in this example is the letter "H," superimposed on a luminance noise background 181B. The second scene 180B in the series has a first target, which in this example is the letter "K," superimposed on a uniform gray field background 182A, and has a second target, which in this example is the letter "N," superimposed on a luminance noise background 182B. The third scene 180C in the series has a first target, which in this example is the letter "N," superimposed on a uniform gray field background 183A, and has a second target, which in this example is the letter "D," superimposed on a luminance noise background 183B. The fourth through seventh scenes 180D, 180E, 180F and 180G have the targets of "Z," "N," "K," and "V," respectively, superimposed on the respective uniform gray field backgrounds 184A, 185A, 186A and 187A, but they may not all be visible depending on the reader's vision. The fourth through seventh scenes 180D, 180E, 180F, and 180G have the targets of "K," "V," "R," and "C," respectively, superimposed on the respective luminance noise backgrounds 184B, 185B, 186B and 187B, but they may not all be visible depending on the reader's vision.

In accordance with a representative embodiment, the level of luminance noise in the luminance noise backgrounds 181B, 182B and 182C remains substantially constant over all of the scenes 180A-180G in the series. Likewise, the uniform gray field background 181A, 182A and 183A remains substantially constant over all of the scenes 180A-180G in the series. In each successively presented scene, the levels of contrast of the first and second targets changes relative to the levels of contrast of the first and second targets, respectively, of the immediately preceding scene (i.e., of the previously presented scene). For example, the first target "K" in the second scene 180B has a lower contrast level than the first target "D" in the first scene 180A. Likewise, the first target "N" in the third scene 180C has a lower contrast level than the first target "K" in the second scene 180B. The second target "N" in the second scene 180B has a lower contrast level than the second target "H" in the first scene 180A. Likewise, the second target "D" in the third scene 180C has a lower contrast level than the second target "N" in the second scene 180B. The level of luminance noise in the luminance noise backgrounds 181B, 182B and 183B remains substantially constant over the first, second and third scenes 180A, 180B and 180C, respectively.

In accordance with a representative embodiment, the first and second targets of each respective scene are different from one another. For example, in scene 180A, the first and second targets are the letter "D" and the letter "H," respectively. In FIG. 5, the second target that is superimposed on the luminance noise background is positioned below and adjacent to the first target of the respective scene, but the first and second targets of each scene can have a variety of relative positions, e.g., the second target can be above instead of below the first target, the first and second targets can be side-by-side, etc.

The eye chart 180 is typically used to test CS as follows. The subject is presented with the eye chart 180 and asked to read the targets in the scenes from left to right, i.e., starting with the left-most scene 180A and ending with the right-most scene 180G. The test may be administered by a doctor or other healthcare person or via an automated process. The subject attempts to correctly identify the targets in the presented scenes and the subject's answers are monitored and/or recorded. The number of first and second targets that are correctly identified and their locations in the sequence are used to assess CS. For example, the total number of targets in the top row that are correctly identified is compared to a normal range for CS in the absence of noise and the number of targets in the bottom row that are correctly identified is compared to a normal range for CS in the presence of noise. The assessed CS may also be used to diagnose particular ailments and diseases, as will be discussed below in more detail.

FIGS. 6A-6L represent pages or screen shots of the noise-based eye chart in accordance with a representative embodiment in which a series of twelve scenes 190A-190L are arranged on respective pages of a book or are displayed as respective screen shots on a display monitor screen, depending on the manner in which the eye chart is implemented. An example of the step represented by block 171 of FIG. 4 will now be provided with reference to FIGS. 6A-6C. For this example, it will be assumed that scenes 190A-190C are on three separate pages of a book, although they could be on the same page of the book or could be displayed as one or more screen shots on a display monitor.

The first scene 190A in the series shown in FIG. 6A has a first target, which in this example is three letters "O," "V" and "H" arranged side-by-side and superimposed on a uniform gray field background 191A, and has a second target, which in this example is three letters "V," "R" and "C" superimposed on a luminance noise background 191B and arranged side-by-side. The second scene 190B in the series shown in FIG. 6B has a first target, which in this example is three letters arranged side-by-side "K," "C" and "H" superimposed on a uniform gray field background 192A, and has a second target, which in this example is three letters "O," "Z" and "V" arranged side-by-side and superimposed on a luminance noise background 192B. The third scene 190C in the series shown in FIG. 19C has a first target, which in this example is three letters arranged side-by-side "C," "K" and "R" superimposed on a uniform gray field background 193A, and has a second target, which in this example is three letters "D," "S" and "N" arranged side-by-side and superimposed on a luminance noise background 193B. It should be noted that every panel shown in FIG. 6 contains three letters arranged side-by-side and superimposed on a uniform gray field background and three letters arranged side-by-side and superimposed on a luminance noise background, although some of the letters may not be visible depending on the reader's vision.

In accordance with a representative embodiment, the level of luminance noise in the luminance noise backgrounds 191B, 192B and 193B remains substantially constant over all of the scenes 190A-190C. Likewise, the uniform gray field background 191A, 192A and 193A remains substantially constant over all of the scenes 190A-190C. In each successively presented scene, the levels of contrast of the first and second targets changes relative to the levels of contrast of the first and second targets, respectively, of the immediately preceding scene (i.e., of the previously presented scene). For example, the first target "K C H" in the second scene 190B has a lower contrast level than the first target "O V H" in the first scene 190A. Likewise, the first target "C K R" in the third scene 190C has a lower contrast level than the first target "K C H" in the second scene 190B. The second target "O Z V" in the second scene 190B has a lower contrast level than the second target "V R C" in the first scene 190A. Likewise, the second target "D S N" in the third scene 190C has a lower contrast level than the second target "O Z V" in the second scene 190B. The level of luminance noise in the luminance noise backgrounds 191B, 192B and 193B remains substantially constant over the first, second and third scenes 190A, 190B and 190C, respectively.

The eye chart 190A-190L is typically used to test CS as follows. The subject is presented with a page of the eye chart containing scene 190A and asked to read the first and second targets in the scene. The subject attempts to correctly identify the targets in the scene and the subject's answers are monitored and/or recorded. This process is performed for each page containing the scenes 190A-190L. The number of first and second targets that are correctly identified and their locations in the sequence are used to assess CS. For example, the total number of targets in the top row that are correctly identified is compared to a normal range for CS in the absence of noise and the number of targets in the bottom row that are correctly identified is compared to a normal range for CS in the presence of noise. The assessed CS may also be used to diagnose particular ailments and diseases of the eye, as will be discussed below in more detail.

With reference again to FIG. 4, block 172 represents the step of monitoring the subject's responses as he or she reads the series of scenes presented. Block 173 represents the step of evaluating the subject's CS based, at least in part, on the subject's responses. It should be noted that the steps of presenting the series of scenes to the subject (box 171), of monitoring the subject's responses (box 172) and of evaluating the subject's CS based, at least in part, on the subject's responses can be performed manually by a doctor or other healthcare worker or they can be partially or entirely automated. An example of automating the process represented by the flow diagram of FIG. 4 is a kiosk having a computer with one or more processors that perform an algorithm that causes screen shots corresponding to scenes 190A-190L to be displayed, a display monitor connected to the computer for displaying the screen shots, and a keyboard or other input device connected to the computer that is used by the subject to make selections when attempting to correctly identify the targets. One or more processors of the computer may be configured to execute one or more algorithms that process the subject's selections to perform the evaluation represented by block 173.

Figure 7:
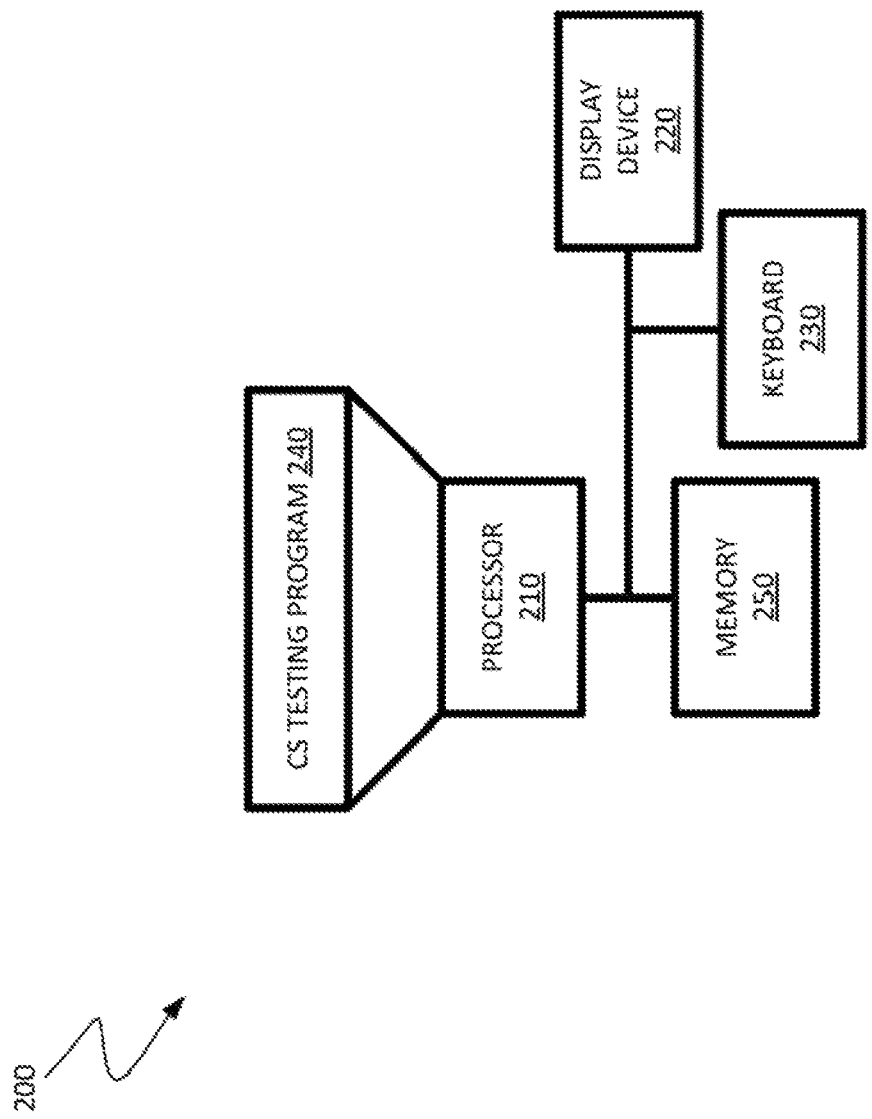
FIG. 7 illustrates a block diagram of computer system configured to perform the method represented by the flow diagram shown in FIG. 4 in accordance with a representative embodiment.

FIG. 7 is a block diagram of a computer system 200 in accordance with an embodiment that can be configured to perform the processes described above with reference to FIG. 4 that are capable of being automated and performed by a computer. A processor 210 of the computer system 200 is configured to execute a CS testing program 240 that displays a sequence of scenes to a subject on a display monitor 220, such as the series of scenes 190A-190L shown in FIGS. 19A-19L, monitors responses made by the subject via a keyboard 230 or some other input device of the computer system 200, and processes the subject's responses to perform the evaluation referred to in block 173 of FIG. 4. The computer system 200 includes a memory 250 that stores computer code corresponding to the CS testing program 240 that is executed by processor 210. The memory 250 may be any suitable non-transitory computer-readable medium, and is typically a solid state memory device, but may be an optical storage device or a magnetic storage device.

In accordance with a representative embodiment, the level of contrast of the targets ranges from about 58 percent to about 0.5 percent. For example, in FIG. 6A the contrast of the letters is 58% and in FIG. 6L the contrast of the letters is 0.5%, with the level of contrast decreasing in steps of 0.15 log units over the course of the series. In accordance with an embodiment, the target contrast decreases in 0.15 log unit steps in successive scenes, although other step-wise increments as well as non-step-wise changes may be used to vary the contrast level. It should be noted that while the representative embodiment have been described with reference to the level of contrast of the targets decreasing in successive scenes, the level of contrast may instead increase in successive scenes such that the targets are more difficult to see earlier in the series and easier to see later in the series.

As indicated above, the first and second targets of each scene can have a variety of relative positions and orientations. In accordance with an embodiment, the first target that is superimposed on the uniform gray field is oriented above the second target that is superimposed on the luminance noise background, as shown in FIG. 5. In accordance with another embodiment, the first target that is superimposed on the uniform gray field is oriented adjacent to the second target that is superimposed on the luminance noise background, as shown in FIGS. 6A-6L.

As indicated above, in accordance with an embodiment, the successive scenes are presented sequentially in book fashion on successive pages, as described above with reference to FIGS. 6A-6L. In accordance with another embodiment, the successive scenes are presented as images adjacent to one another on a single page or chart, as shown in FIG. 5.

In accordance with an embodiment, the results of the test are scored by: 1) comparing the number of correctly identified first targets and second targets to normal reference ranges; 2) comparing the difference between the number of correctly identified first targets and second targets to a normal reference range. This novel metric provides a measure of 1) absolute CS in the absence of noise; 2) absolute CS in the presence of a fixed noise level; and 3) the effect of noise on CS (the difference between 1 and 2). These three measures may provide a signature of different eye diseases, such that patients with one disease (e.g., DR) will perform differently than patients with another disease (e.g. glaucoma). The test in accordance with the present disclosure exceeds the sensitivity of current chart-based CS tests, such as those described above with reference to FIGS. 1-3.

In the case in which the noise-based eye chart is implemented as a book, the book can be relatively inexpensive, compact, portable, and insensitive to room illumination (i.e., the effects of room illumination are negligible, within reason). All of these goals can be achieved by making the book relatively small in size. The size of the book may be, for example, 9" inch (22.86 centimeters (cm)) width by 7" (17.78 cm) in height. Keeping the book relatively small in size makes the scenes insensitive to the room lighting conditions, which cannot be said of the known eye charts described above with reference to FIGS. 1-3. Doubling the size of the book to, for example, 18" in width by 14" in height would not affect its insensitivity to room lighting conditions, but making the book much larger in size than that would make it sensitive to room lighting conditions.

The noise-based eye chart may also be used for disease specificity, i.e., to distinguish between different causes of CS losses. For example, CS loss in the absence of noise with normal CS in the presence of noise is characteristic of patients who have DR and RP, whereas CS loss in both the presence and absence of noise may be associated with amblyopia.

| No Noise CS (bottom): | In Noise CS (top): | |
| --- | --- | --- |
| Normal | Normal | Visually-normal individual |
| Abnormal | Abnormal | Amblyopia; Juvenile x-linked retinoschisis; Moderate-late stage glaucoma |
| Abnormal | Normal | Retinitis pigmentosa; Diabetic retinopathy |
| Normal | Abnormal | Early glaucoma |

The table above provides possible outcomes and diseases that may be associated with the outcomes using the noise-based eye chart shown in FIGS. 6A-6L to assess CS in a subject. The first column in the table lists different outcomes that can occur when testing CS in the absence of noise based on the subject's responses when reading the bottom rows of letters in scenes 190A-190L. The second column in the table lists different outcomes that can occur when testing CS in the presence of noise based on the subject's responses when reading the top rows of letters in scenes 190A-190L. The third column in the table lists the diseases that may be associated with the outcomes. For example, if results of the test are that the subject has normal CS in the absence of noise and abnormal CS in the presence of noise, the corresponding row in the third column indicates that the outcomes are indicative of early glaucoma.

In addition, because CS in noise is not affected by cataract (within reason), comparison of CS in the presence and absence of noise may help predict the potential for improvement following cataract surgery. For example, CS in noise loss in a cataract patient suggests that there is an additional retina or optic nerve defect that is limiting CS. As such, removing the cataract will not likely restore CS to normal.

It should be noted that the inventive principles and concepts have been described with reference to representative embodiments, but that the inventive principles and concepts are not limited to the representative embodiments described herein. Although the inventive principles and concepts have been illustrated and described in detail in the drawings and in the foregoing description, such illustration and description are to be considered illustrative or exemplary and not restrictive; the invention is not limited to the disclosed embodiments. Other variations to the disclosed embodiments can be understood and effected by those skilled in the art, from a study of the drawings, the disclosure, and the appended claims.

What is claimed is:

1. A diagnostic tool for assessing contrast sensitivity in a subject, the diagnostic tool comprising:
   a series of scenes to be presented to the subject, each scene comprising at least a first target having a preselected level of contrast superimposed on a uniform background and a second target having a preselected level of contrast superimposed on a luminance noise background, wherein in each successively presented scene the first and second targets that are superimposed on the uniform background and on the luminance noise background, respectively, have contrast levels that are different from the contrast levels of the first and second targets superimposed on the uniform background and on the luminance noise background, respectively, in a previously presented scene.

2. The diagnostic tool of claim 1, wherein the diagnostic tool comprises a book having a cover and a plurality of pages arranged within the cover, each page having at least one of the series of scenes disposed thereon.

3. The diagnostic tool of claim 1, wherein the diagnostic tool comprises at least one sheet or substrate having a plurality of the series of scenes disposed thereon.

4. The diagnostic tool of claim 1, wherein the uniform background is a uniform gray field background.

5. The diagnostic tool of claim 1, wherein the luminance noise background has a substantially constant level of luminance noise over the series of scenes.

6. The diagnostic tool of claim 1, wherein the preselected level of contrast of the first target of each scene ranges from 58 percent to 0.5 percent over the series of scenes.

7. The diagnostic tool of claim 6, wherein the preselected level of contrast of the second target of each scene ranges from 58 percent to 0.5 percent over the series of scenes.

8. The diagnostic tool of claim 1, wherein in at least a first scene of the series of scenes, the preselected level of contrast of the first target and the preselected level of contrast of the second target are equal to a first level of contrast.

9. The diagnostic tool of claim 8, wherein in at least a second scene of the series of scenes that is presented to the subject in immediate succession to the first scene being presented to the subject, the preselected level of contrast of the first target and the preselected level of contrast of the second target are equal to a second level of contrast.

10. The diagnostic tool of claim 9, wherein the second level of contrast is less than the first level of contrast.

11. The diagnostic tool of claim 9, wherein the second level of contrast is greater than the first level of contrast.

12. The diagnostic tool of claim 2, wherein the book has a size that is less than or equal to nine inches by seven inches, respectively, and wherein the size of the book makes the scenes generally insensitive to the room lighting conditions.

13. A method of assessing contrast sensitivity in a subject comprising:
   i) presenting to a subject a series of scenes, each scene comprising at least a first target having a preselected level of contrast superimposed on a uniform background and a second target having a preselected level of contrast superimposed on a luminance noise background, wherein in each successively presented scene the first and second targets that are superimposed on the uniform background and on the luminance noise background, respectively, have contrast levels that are different from the contrast levels of the first and second targets superimposed on the uniform background and on the luminance noise background, respectively, in a previously presented scene;
   ii) monitoring responses by the subject to step i); and
   iii) evaluating the contrast sensitivity of the subject based on the monitored responses.

14. The method of claim 13, wherein the uniform background is a uniform gray field background.

15. The method of claim 13, wherein the luminance noise background has a substantially constant level of luminance noise over the series of scenes.

16. The method of claim 13, wherein the preselected level of contrast of the first target of each scene ranges from 58 percent to 0.5 percent over the series of scenes.

17. The method of claim 14, wherein the preselected level of contrast of the second target of each scene ranges from 58 percent to 0.5 percent over the series of scenes.

18. The method of claim 13, wherein in at least a first scene of the series of scenes, the preselected level of contrast of the first target and the preselected level of contrast of the second target are equal to a first level of contrast.

19. The method of claim 18, wherein in at least a second scene of the series of scenes that is presented to the subject in immediate succession to the first scene being presented to the subject, the preselected level of contrast of the first target and the preselected level of contrast of the second target are equal to a second level of contrast.

20. The method of claim 13, wherein step i) is performed by a computer system having one or more processors that perform one or more algorithms to cause the series of scenes to be displayed on a display monitor of the computer system, and wherein step ii) is performed by the computer system by receiving as input selections made by the subject on an input device of the computer system, the selections corresponding to the responses.

* * * * *